United States Patent
Summers et al.

(10) Patent No.: US 12,129,503 B2
(45) Date of Patent: *Oct. 29, 2024

(54) CARBON SEQUESTRATION IN SOILS WITH PRODUCTION OF CHEMICAL PRODUCTS

(71) Applicant: LanzaTech, Inc., Skokie, IL (US)

(72) Inventors: Zarath Morgan Summers, Prospect Heights, IL (US); Sean Dennis Simpson, Evanston, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/446,758

(22) Filed: Aug. 9, 2023

(65) Prior Publication Data

US 2024/0052377 A1    Feb. 15, 2024

Related U.S. Application Data

(60) Provisional application No. 63/370,988, filed on Aug. 10, 2022.

(51) Int. Cl.
| | |
|---|---|
| C12M 1/107 | (2006.01) |
| C12M 1/00 | (2006.01) |
| C12N 1/20 | (2006.01) |
| C12N 1/22 | (2006.01) |
| C12N 1/32 | (2006.01) |
| C12P 7/04 | (2006.01) |
| C12P 7/06 | (2006.01) |
| C12P 7/10 | (2006.01) |

(52) U.S. Cl.
CPC .......... *C12P 7/10* (2013.01); *C12N 1/20* (2013.01); *C12N 1/22* (2013.01); *C12N 1/32* (2013.01)

(58) Field of Classification Search
CPC ...... C12P 7/10; C12P 7/04; C12P 7/06; C12P 15/74; C12N 1/22; C12N 1/32; C12M 21/04

See application file for complete search history.

(56) References Cited

U.S. PATENT DOCUMENTS

| | | |
|---|---|---|
| 1,128,549 A | 2/1915 | Godfrey |
| 1,408,091 A | 2/1922 | Kellam |
| 2,099,090 A | 11/1937 | Webb |
| 2,405,986 A | 8/1946 | Sullivan |
| 3,020,708 A | 2/1962 | Mahan |
| 3,102,875 A | 9/1963 | Heiss |
| 4,692,168 A | 9/1987 | Dotson |
| 5,173,429 A | 12/1992 | Gaddy |
| 5,593,886 A | 1/1997 | Gaddy |
| 6,368,819 B1 | 4/2002 | Gaddy |
| 6,811,769 B2 | 11/2004 | Watanabe |
| 10,856,560 B2 | 12/2020 | Simpson |
| 11,827,916 B2 * | 11/2023 | Foody ............... C07C 29/1518 |
| 2009/0139139 A1 | 6/2009 | Tilman et al. |
| 2013/0230609 A1 | 9/2013 | Modak |
| 2014/0377828 A1 | 12/2014 | Rodriguez et al. |
| 2018/0334690 A1 | 11/2018 | Burk et al. |
| 2020/0165733 A1 | 5/2020 | Reed et al. |
| 2021/0198702 A1* | 7/2021 | Foody ............... C10G 2/50 |
| 2021/0371312 A1 | 12/2021 | Conrado et al. |

FOREIGN PATENT DOCUMENTS

| | | |
|---|---|---|
| EP | 117309 A1 | 9/1984 |
| WO | 1992008555 A1 | 5/1992 |
| WO | 1997010331 A1 | 3/1997 |
| WO | 9800558 A1 | 1/1998 |
| WO | 0068407 A1 | 11/2000 |
| WO | 0208438 A2 | 1/2002 |
| WO | 2006088491 A2 | 8/2006 |
| WO | 2007115157 A2 | 10/2007 |
| WO | 2007117157 A1 | 10/2007 |
| WO | 2008115080 A1 | 9/2008 |
| WO | 2009151342 A1 | 12/2009 |
| WO | 2011034887 A2 | 3/2011 |
| WO | 2011112103 A1 | 9/2011 |
| WO | 2012024522 A2 | 2/2012 |
| WO | 2012026833 A1 | 3/2012 |
| WO | 2012115527 A2 | 8/2012 |
| WO | 2013036147 A2 | 3/2013 |
| WO | 2013180581 A1 | 12/2013 |
| WO | 2013180584 A1 | 12/2013 |
| WO | 2013185123 A1 | 12/2013 |

(Continued)

OTHER PUBLICATIONS

Abrini et al., Archives of Microbiology 161, 1994, pp. 345-351.
Chi et al. (2011), "Oleaginous yeast Cryptococcus curvatus culture with dark fermentation hydrogen production effluent as feedstock for microbial lipid production," International Journal of Hydrogen Energy, 36:9542-9550.
Demler et al., "Reaction Engineering Analysis of Hydrogenotrophic Production of Acetic Acid by Acetobacterium woodii," Biotechnology and Bioengineering, vol. 108, No. 2, Feb. 2011.
Klasson, et al. (1991), Bioreactor design for synthesis gas fermentations, Fuel, 70:605-614.
Klasson, et al. (1991), Bioreactors for synthesis gas fermentations resources, Conservation and Recycling, 5:145-165.

(Continued)

*Primary Examiner* — Maryam Monshipouri

(57) ABSTRACT

Improving overall carbon capture specially carbon sequestration in soil and improving overall production yield of bio-derived chemical products and fuels by integrating microbial fermentation into nature-based solutions and natural climate solutions. Converting feedstock of biomass and optionally supplemental bio-derived material, wherein the biomass comprises harvested biodiverse above-ground plant material comprising at least about 2, 3, 5, 8, 10, 12, 15 or 20 different species of plants from an area of land wherein the biodiverse above-ground plant material is harvested no more than one, two, or three times in a 12-month period of time to one or more products. In certain aspects, also disclosed are to processes for producing desirable products, such as ethylene, from biodiverse biomass.

16 Claims, 5 Drawing Sheets

(56) References Cited

FOREIGN PATENT DOCUMENTS

| WO | 2013191567 A1 | 12/2013 |
| WO | 2014036152 A1 | 3/2014 |
| WO | 2014100851 A1 | 7/2014 |
| WO | 2015073854 A2 | 5/2015 |
| WO | 2016094334 A1 | 6/2016 |
| WO | 2016191625 A1 | 12/2016 |
| WO | 2017066498 A1 | 4/2017 |
| WO | 2017161387 A1 | 9/2017 |
| WO | 2019126400 A1 | 6/2019 |

OTHER PUBLICATIONS

Klasson, et al. (1992), Bioconversion of synthesis gas into liquid or gaseous fuels, Enzyme and Microbial Technology, 14:602-608.

Lewis et al (2002), Making the connection-conversion of biomass-generated producer gas to ethanol, Abst. Bioenergy, p. 2091-2094.

Liou et al., International Journal of Systematic and Evolutionary Microbiology 33, 2005, pp. 2085-2091.

Martin, et al., Dissimilation of Carbon Monoxide to Acetic Acid by Glucose-Limited Cultures of Clostridium thermoaceticum, Applied and Environmental Microbiology, 49(6), 1985, 1412-1417.

Najafpour and Younesi (2006) Ethanol and acetate synthesis from waste gas using batch culture of Clostridium ljungdahlii. Enzyme and Microbial Technology, 38(1-2):223-228.

Sakai et al., Biotechnology Letters 26, 2004, pp. 1607-1612.

Sanchez, Daniel, "Market Criteria for Carbon Farming Pathways" presented Jun. 29, 2022, at Carbon Farming Workshop by ARPA-E within the US Department of Energy Jun. 28-29, 2022, at Kansas City, MO.

Sipma et. al. Critical Reviews in Biotechnology, 2006, vol. 26. pp. 41-65.

Speight, James G. Handbook of Petroleum Refining. Taylor & Francis, 2017.

Svetlichny, V. A., et al. (1991), Systematic and Applied Microbiology 14: 254-260.

Vega, et al. (1989), Study of gaseous substrate fermentations: Carbon monoxide conversion to acetate. 1. Batch culture, Biotech. Bioeng., 34(6):774-784.

Vega, et al. (1989), Study of Gaseous Substrate Fermentation: Carbon Monoxide Conversion to Acetate. 2. Continuous Culture, Biotech. Bioeng., 34(6):785-793.

Vega, et al. (1990), Design of Bioreactors for Coal Synthesis Gas Fermentations, Resources, Conservation and Recycling, 3:149-160.

International Search Report and Written Opinion issued in International Application No. PCT/US2023/071897, dated Nov. 22, 2023, 11 pages.

* cited by examiner

CARBON SEQUESTRATION IN SOILS WITH PRODUCTION OF CHEMICAL PRODUCTS

CROSS REFERENCE TO RELATED APPLICATIONS

This application claims the benefit of U.S. Provisional Patent Application No. 63/370,988 filed on Aug. 10, 2022, the entirety of which is incorporated herein by reference.

FIELD

The present disclosure relates to improving carbon sequestration in soils while also producing chemical products by microbial fermentation. The disclosure presents a method to converts specific carbon sources that stimulate carbon sequestration in soils to one or more products. More specifically, the present disclosure relates to methods for integrating gas fermentation into a nature-based economy that reduces atmospheric carbon, drives carbon sequestration in soils, while at the same time generates valuable profitable chemical products and fuels.

BACKGROUND

The following discussion is provided to aid the reader in understanding the disclosure and is not admitted to describe or constitute prior art thereto.

Carbon (C) sequestration refers to the storage of carbon into a stable form. Plant photosynthesis uses sunlight to combine carbon dioxide ($CO_2$) from the air and water ($H_2O$) to form glucose ($C_6H_{12}O_6$), a simple sugar that is stored within the tissue of living plants; and indirectly, by the microbial decomposition of the biomass of plant and animal tissue into other compounds such as carbohydrates, proteins, organic acids, humic substances, waxes, coal, oil, and natural gas, etc. Combined together, these organic compounds essentially act to "hold soil together" and is how soil attains its fertility. The higher the content of soil organic carbon (SOC), the greater the fertility and productivity of the soil. This large soil carbon sink is a desirable method of sequestering carbon and removing $CO_2$ from the atmosphere.

In an effort to sequester more atmospheric carbon into soil organic matter, the Soil Science Society of America, the American Society of Agronomy, and other world scientific organizations have relied and advocated for farmers to grow crops using practices that include: no till or reduced tillage; crop rotation; the use of cover crops; fertility management; and water management (as it pertains to the amount used), etc., as being the "primary tools" and overall strategy to accomplish that goal. While these methods can be helpful and on the "right track", their ability to sequester more net atmospheric carbon into soil organic carbon, both separately and as a whole, is extremely limited because the actual process of growing crops and supplying the necessary plant biomass itself mechanically disturbs the soil through tilling and aeration to break up bicarbonate buildup. In the process of mechanically disturbing the soil, as for example, tilling the soil to loosen carbonate clogged pores of the soil to increase water soil penetration, the process turns and exposes what soil organic carbon there is and makes it susceptible to erosion and die off through exposure to sunlight, heat, and wind, causing large portions of the soil carbon pool to diminish or become lost.

Land-use changes associated with agriculture can disrupt the natural balance between the production of carbon-containing biomass and the release of carbon by soil respiration. Some suggest that this imbalance alone results in an annual net release of $CO_2$ to the atmosphere from agricultural soils equal to about 20 percent of the current annual release of $CO_2$ from the burning of fossil fuels. Agricultural practices in temperate zones, for example, can result in a decline of soil organic matter that ranges from 20 to 40 percent of the original content after about 50 years of cultivation. Although a portion of this loss can be attributed to soil erosion, the majority is from an increased flux of carbon to the atmosphere as $CO_2$. Consequently, more often than not, a net loss of soil carbon results from mechanical tillage methods alone.

Another approach is to increase carbon sequestration by applying strong mineral acids to break down the carbonate/bicarbonate soil deposits. These strong mineral acids, such as hydrochloric acid, sulfuric acid, and phosphoric acid have no buffering capability, and if not applied in the right dilution actually shock the soil and release $CO_2$ directly into the atmosphere as the soil carbonates/bicarbonates react to the strong acid rather than dissolving as bicarbonates into the aqueous fraction. Low acid pH applications of around 1 to 2 are also damaging to plant roots and soil bacteria so that further uptake of $CO_2$ is adversely affected creating a soil dead zone. In addition, some of these strong mineral acids, such as hydrochloric acid, increase the chloride concentration in the soil exacerbating harmful saline salt buildup. Current methods provide only a partial solution at best and cannot be relied upon as the sole means to restore and/or sequester more organic carbon back into the soil.

Gas fermentation processes can be used to generate target materials from synthesis gas, known as syngas. Syngas is a mixture of hydrogen and carbon monoxide and often contains some $CO_2$ and methane. Syngas may be generated though processing of carbon-based materials such as methane. For example, particular biological systems can be used to perform gas fermentation.

Additionally, many domestic and international governmental entities are placing tighter restrictions on the total amount of carbon that a particular site, complex, or entity is allowed to release into the atmosphere. Such restrictions are pushing industrial, commercial, and agricultural operators alike to pursue and implement expensive efficiency upgrades to already well-developed technologies within their respective fields.

Similarly, solid waste material is often carbon rich and can be gasified to form syngas, which then becomes a substrate for gas fermentation. What is presently a waste material to be disposed of can be converted by a gas fermentation system which also comprises an optional gasifier to become a valuable product. In this way, carbon is recycled from a useful article which has reached the end of its life into new carbon components to manufacture new articles or products. Existing fossil carbon may be continuously recycled to create new carbon-based products without the need for additional fossil carbon. Similarly, non-fossil carbon, such as modern carbon, may also be recycled.

Although gas fermentation processes can be used for carbon capture and other applications, gas fermentation could be more widely implemented if cost barriers of constructing and maintaining the infrastructure necessary to transport either the carbon source to a gas fermentation process or transporting the products generated by the gas fermentation processes out to a buyer. For example, where a gas fermentation process produces a gas stream containing ethylene, the ethylene stream could be transported to existing ethylene refining and purification assets using established product transportation infrastructure, such as the network of natural gas pipelines. In so doing, the capital and operating costs of new sustainable ethylene production facilities could be minimized while also decreasing the carbon footprint of ethylene production. Thus, integration of gas fermentation systems with existing chemical transportation infrastructure enables increased adoption of sustainable chemical production in a dispersed fashion where appropriately sized GF systems may be located near to such infrastructure into order to readily transport sustainable products to locations of demand.

SUMMARY

Described herein are systems and methods for incorporating gas fermentation into nature-based solutions (NIBS) and natural climate solutions (NCS) to convert biodiverse biomass feedstocks into useful products, such as ethylene, ethanol, and the like while also sequestering carbon in the soil and generating CERCs.

In a first aspect, the present disclosure provides methods of introducing a feedstock to an anerobic digestion zone to generate at least a biogas effluent comprising methane, wherein the feedstock comprises biomass and optionally supplemental bio-derived material, and wherein the biomass comprises harvested biodiverse above-ground plant material comprising at least about 2, 3, 5, 8, 10, 12, 15 or 20 different species of plants from an area of land wherein the biodiverse above-ground plant material is harvested no more than one, two, or three times in a 12 month period of time; passing a stream comprising oxygen and at least a portion of the biogas effluent to a methane conversion zone operating at methane conversion conditions to generate a syngas stream comprising $CO_2$, CO, and $H_2$; passing the syngas stream to a microbial gas fermentation zone comprising at least one C1 fixing microorganism and a nutrient solution in at least one bioreactor; culturing the C1 fixing microorganism in the bioreactor by fermentation to generate a fermentation broth comprising at least one chemical product; and separating the at least one chemical product from the fermentation broth.

In some embodiments, the area of land is grasslands.

In some embodiments, area of land is prairie.

In some embodiments, the supplemental bio-derived material is animal waste, agricultural waste, forestry waste, sewage, food waste, brewery grain byproducts, organic industry waste, seaweed, plankton, algae, fish, fish waste, potato waste, sugar cane waste, sugar beet waste, straw, paper waste, manure, sawdust, wood, leaves, vegetables, nut shells, cotton trash, rice hulls, orange peels, poultry lotter, dairy manure, paper sludge, sewage sludge, sawdust, wood, leaves, vegetables, nut shells, straw, cotton trash, rice hulls, orange peels, poultry litter, dairy manure, other manures, paper sludge, distillers grain, and sewage sludge, residential compost, industrial compost or any combinations thereof.

In some embodiments, the ratio of biodiverse biomass and supplemental bioderived material varies according to when the biodiverse biomass is harvested.

In some embodiments, the anerobic digestion zone, the methane conversion zone and the gas fermentation zone are co-located with the area of land or a source of the supplemental bioderived material, or both.

In some embodiments, the anerobic digestion zone, the methane conversion zone, and the gas fermentation zone and the area of land are within 1 mile, within 2 miles, within 3 miles, within 4 miles, or within 5 miles of each other.

In some embodiments, the feedstock does not undergo a drying procedure before introducing to an anerobic digestion zone.

In some embodiments, the anerobic digestion zone, the methane conversion zone and the gas fermentation zone are co-located with the area of land wherein the biodiverse above ground plant material is harvested.

In some embodiments, the anerobic digestion zone, the methane conversion zone and the gas fermentation zone are located remote from the area of land wherein the biodiverse above ground plant material is harvested.

In some embodiments solids are generated in the anerobic digestion zone for use as soil amendments.

In some embodiments, the C1-fixing microorganism is aerobic or anaerobic.

In some embodiments, the C1-fixing microorganism is selected from a genus of *Clostridium, Moorella, Carboxydothermus, Ruminococcus, Acetobacterium, Eubacterium, Butyribacterium, Oxobacter, Methanosarcina, Methanosarcina, Desulfotomaculum*, and *Cupriavidus*.

In some embodiments, the method further comprising the step of determining the mass of the gas fermentation product, the mass of the feedstock, or both.

In some embodiments, the at least one product is selected from an alcohol, an acid, a diacid, an alkene, a terpene, an isoprene, and alkyne.

In some embodiments, the gas fermentation product is selected from ethylene, ethanol, propane, acetate, 1-butanol, butyrate, 2,3-butanediol, lactate, butene, butadiene, methyl ethyl ketone (2-butanone), acetone, isopropanol, a lipid, 3-hydroxypropionate (3-HP), a terpene, isoprene, a fatty acid, 2-butanol, 1,2-propanediol, 1propanol, 1hexanol, 1octanol, chorismate-derived products, 3hydroxybutyrate, 1,3butanediol, 2-hydroxyisobutyrate or 2-hydroxyisobutyric acid, isobutylene, adipic acid, 1,3hexanediol, 3-methyl-2-butanol, 2-buten-1-ol, isovalerate, isoamyl alcohol, and monoethylene glycol, or any combination thereof.

In some embodiments, the method further comprising generating a first wastewater stream from the anaerobic digestion zone and a second wastewater stream from the gas fermentation zone and treating both the first and second wastewater streams in a wastewater treatment system.

In some embodiments, the harvested biodiverse aboveground plant material resulted in the stimulation of the sequestration of atmospheric $CO_2$ below ground in the soil.

In some embodiments, the harvested biodiverse aboveground plant material resulted in the stimulation of the sequestration of atmospheric $CO_2$ below ground in the soil and the generation of Carbon Emission Reduction Credits.

In some embodiments, the harvested biodiverse aboveground plant material resulted in the stimulation of the sequestration of atmospheric $CO_2$ below ground in the soil and the generation of measured Carbon Emission Reduction Credits.

In some embodiments, the method further comprising providing the at least one chemical product to a chemical processing facility.

In some embodiments, the method further comprising passing the at least one chemical product to a chemical processing facility selected from an olefins plant, a polyolefins plant, a polypropylene plant, a polyethylene plant, a polymer plant, a high-density polyethylene plant, an oligomers plant, a nitriles plant, an oxides plant, a topping refinery, a hydro-skimming refinery, a conversion refinery, a deep conversion refinery, a coking unit, a stream cracker, or a styrenics plant.

In some embodiments the chemical processing facility is co-located with the anerobic digestion zone, the methane conversion zone, and the gas fermentation zone.

In some embodiments, the anerobic digestion zone, the methane conversion zone, and the gas fermentation zone and the chemical processing facility are within 1 mile, within 2 miles, within 3 miles, within 4 miles, or within 5 miles of each other.

In some embodiments, the method further comprising storing the at least one product.

In another aspect, the present disclosure provides a method of generating a feedstock for a system comprising an anerobic digestion zone, a methane conversion zone and a gas fermentation zone, the method comprising: harvesting a biodiverse biomass of above-ground plant material comprising at least about 2, 3, 5, 8, 10, 12, 15 or 20 different species of plants from an area of land wherein the harvesting is conducted no more than one, two, or three times in a 12-month period of time; and providing the harvested biodiverse biomass of above-ground plant material for use in a system comprising an anerobic digestion zone, a methane conversion zone and a gas fermentation zone.

In some embodiments, the area of land is grasslands.

In some embodiments, the area of land is prairie.

In some embodiments, the harvesting stimulates the sequestration of atmospheric $CO_2$ below ground in the soil.

In some embodiments, the sequestration of atmospheric $CO_2$ below ground in the soil results in the generation of Carbon Emission Reduction Credits.

In some embodiments, the method further comprising calculating Carbon Emission Reduction Credits based on the amount of atmospheric $CO_2$ sequestered below ground in the soil and providing the calculated Carbon Emission Reduction Credits to an approved regulatory agency.

In some embodiments, the method further comprising measuring the amount of $CO_2$ sequestered below ground in the soil.

In some embodiments, the anerobic digestion zone, the methane conversion zone and the gas fermentation zone are co-located with the area of land wherein the biodiverse above ground plant material is harvested.

In some embodiments, the anerobic digestion zone, the methane conversion zone and the gas fermentation zone are located remote from the area of land wherein the biodiverse above ground plant material is harvested.

In some embodiments, the method further comprising the step of determining the mass of the harvested diverse biomass.

In some embodiments, the method further comprising the step of determining the Carbon Emission Reduction Credit resulting from the sequestration of carbon in the soil.

In some embodiments, the anerobic digestion zone, the methane conversion zone, and the gas fermentation zone are co-located with the area of land.

In some embodiments, the anerobic digestion zone, the methane conversion zone, and the gas fermentation zone and the area of land are within 1 mile, within 2 miles, within 3 miles, within 4 miles, or within 5 miles of each other.

The foregoing general description and following detailed description are exemplary and explanatory and are intended to provide further explanation of the disclosure as claimed. Other objects, advantages, and features will be apparent to those skilled in the art from the following brief description of the drawings and detailed description of the disclosure.

DETAILED DESCRIPTION

Figure 1:
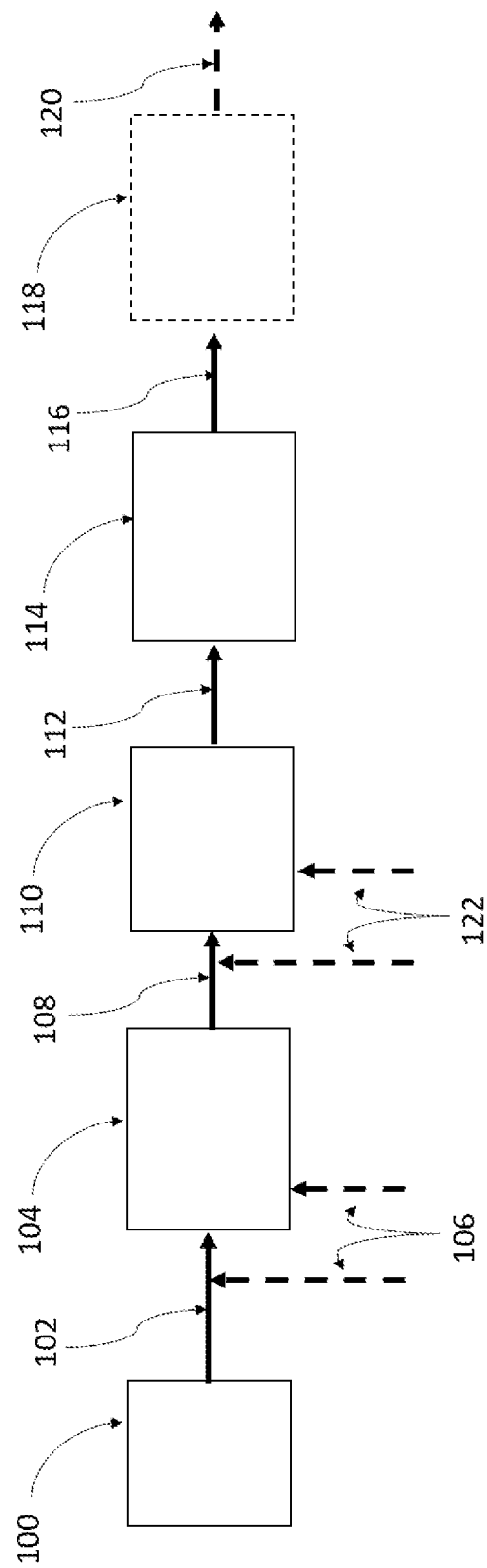
FIG. 1 is an overview of the associated components of an embodiment of a gas fermentation process integrated with a natural climate or nature-based solution.

The present disclosure provides systems and methods for improving carbon capture and reducing the overall carbon that is discarded by integrating into new or existing natural climate solution (NCS) or nature-based solution (NBS) infrastructure microbial fermentation that converts carbon sources that would otherwise be vented to the atmosphere or discarded as waste to one or more products. More specifically, the present disclosure relates to systems and methods for incorporating gas fermentation into NCS or NBS to convert biomass, solid waste, liquid waste, waste gas, and other feedstocks or carbon sources into useful products, such as ethylene, ethanol, and the like.

A. Definitions

It is to be understood that the terminology used herein is for the purpose of describing particular embodiments only and is not intended to be limiting.

Technical and scientific terms used herein have the meanings commonly understood by one of ordinary skill in the art, unless otherwise defined. Unless otherwise specified, materials and/or methodologies known to those of ordinary skill in the art can be utilized in carrying out the methods described herein, based on the guidance provided herein.

As used herein, the singular terms "a," "an," and "the" include plural referents unless the context clearly dictates otherwise. Reference to an object in the singular is not intended to mean "one and only one" unless explicitly so stated, but rather "one or more."

As used herein, "about" when used with a numerical value means the numerical value stated as well as plus or minus 10% of the numerical value. For example, "about 10" should be understood as both "10" and "9-11."

Also as used herein, "and/or" refers to and encompasses any and all possible combinations of one or more of the associated listed items, as well as the lack of combinations when interpreted in the alternative ("or").

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "carbon capture" as used herein refers to the fixation and utilization of carbon including carbon from $CO_2$, CO, and/or $CH_4$ from a stream comprising $CO_2$, CO, and/or $CH_4$ and converting the $CO_2$, CO, and/or $CH_4$ into useful products.

The term "substrate comprising carbon monoxide" and like terms should be understood to include any substrate in which carbon monoxide is available to one or more strains of bacteria for growth and/or fermentation, for example.

The term "gaseous substrates comprising carbon monoxide" includes any gas which contains carbon monoxide. The gaseous substrate will typically contain a significant proportion of CO, preferably at least about 5% to about 100% CO by volume.

The term "C1 carbon" and like terms should be understood to refer to carbon sources that are suitable for use by a microorganism, particularly those of the gas fermentation process disclosed herein. C1 carbon may include, but should not be limited to, carbon monoxide (CO), carbon dioxide ($CO_2$), and methane ($CH_4$), methanol ($CH_3OH$), and formate (HCOOH).

The term "substrate comprising carbon dioxide" and like terms should be understood to include any substrate in which carbon dioxide is available to one or more strains of bacteria for growth and/or fermentation, for example.

The term "gaseous substrates comprising carbon dioxide" includes any gas which contains carbon dioxide. The gaseous substrate will typically contain a significant proportion of $CO_2$, preferably at least about 5% to about 100% $CO_2$ by volume.

The term "bioreactor" includes a fermentation device consisting of one or more vessels and/or towers or piping arrangements, which includes the continuous stirred tank reactor (CSTR), immobilized cell reactor (ICR), trickle bed reactor (TBR), bubble column, gas lift fermenter, membrane reactor such as hollow fiber membrane bioreactor (HFMBR), static mixer, or other vessel or other device suitable for gas-liquid contact.

The term "co-substrate" refers to a substance that, while not necessarily being the primary energy and material source for product synthesis, can be utilized for product synthesis when added to another substrate, such as the primary substrate.

The term "directly", as used in relation to the passing of industrial off or gases to a bioreactor, is used to mean that no or minimal processing or treatment steps, such as cooling and particulate removal are performed on the gases prior to them entering the bioreactor (note: an oxygen removal step may be required for anaerobic fermentation).

The terms "fermenting," "fermentation process," "fermentation reaction," and like terms as used herein, are intended to encompass both the growth phase and product biosynthesis phase of the process. As is described further herein, in some embodiments the bioreactor may comprise a primary bioreactor and a secondary bioreactor.

The term "nutrient medium" as used herein should be understood as the solution added to the fermentation broth containing nutrients and other components appropriate for the growth of the microorganism culture.

The terms "primary bioreactor" or "first reactor" as used herein this term is intended to encompass one or more reactors that may be connected in series or parallel with a secondary bioreactor. The primary bioreactors generally use anaerobic or aerobic fermentation to produce a product (e.g., ethylene, ethanol, acetate, etc.) from a gaseous substrate.

The terms "secondary bioreactor" or "second reactor" as used herein are intended to encompass any number of further bioreactors that may be connected in series or in parallel with the primary bioreactors. Any one or more of these further bioreactors may also be connected to a further separator.

The term "stream" is used to refer to a flow of material into, through and away from one or more stages of a process, for example, the material that is fed to a bioreactor. The composition of the stream may vary as it passes through particular stages. For example, as a stream passes through the bioreactor.

The terms "feedstock" when used in the context of the stream flowing into a gas fermentation bioreactor (i.e., gas fermenter) or "gas fermentation feedstock" should be understood to encompass any material (solid, liquid, or gas) or stream that can provide a substrate and/or C1-carbon source to a gas fermenter or bioreactor either directly or after processing of the feedstock.

The term "waste gas" or "waste gas stream" may be used to refer to any gas stream that is either emitted directly, flared with no additional value capture, or combusted for energy recovery purposes.

The terms "synthesis gas" or "syngas" refers to a gaseous mixture that contains at least one carbon source, such as carbon monoxide (CO), carbon dioxide ($CO_2$), or any combination thereof, and, optionally, hydrogen ($H_2$) that can used as a feedstock for the disclosed gas fermentation processes and can be produced from a wide range of carbonaceous material, both solid and liquid.

B. Disclosed Systems and Methods

The development of a vibrant economy requires a safe and healthy food supply, sustainable land use, clean water, and pure air, among other things. Producers, such as farmers and ranchers offset their production costs with income derived from products such as grain, hay, and meat. State and Federal regulations provide few penalties for non-point sources of pollution, so the costs for sub-optimal land use are transferred to the public in the form of remediation costs, while the value of benefits realized by society for optimal land use does not reach the producer.

A major barrier to the development of a nature-based economy is lack of financial certainty from employing certain land management practices, measurable impacts on soil, air, and water quality and environmental regulations. The present disclosure operates to "de-risk" investments in certain land management practices by generating additional high value and profitable chemical products and fuels as a direct result of practices that stimulate carbon sequestration in soil. Climate driven land management practices coupled with market-driven management strategies that produce commodities embody attributes of value to society while also maximizing return on investment though generating a valuable profitable feedstock and valuable profitable chemical and fuel products.

An example of environmental attributes achievable is Carbon Emission Reduction Credits. An accelerating rate of change in the amounts of trace gases in the earth's atmosphere has the potential to modify the earth's energy balance, which may result in a variety of consequences. These trace gases are often referred to as greenhouse gases and include carbon dioxide. There is widespread agreement in the global community that it is prudent to enact policies to attempt to slow down the rate of change. At the same time, research is underway to predict the consequences of increasing greenhouse gas concentrations and to develop the technology to economically limit those increases. All current protocols have established emission reduction targets that define a specific base year, e.g., 1990, and specify reductions as a fractional percentage of emission rates from those of the base year.

The increasing concentration of greenhouse gases in the atmosphere is a global issue. For example, carbon dioxide emitted from a power plant into the atmosphere has a lifetime of approximately 100 years and may be distributed globally. As a result, at least for the issue of atmospheric greenhouse gases, the geographic location where the greenhouse gases are removed from the atmosphere is less important than the fact that they are removed. For other types of EBCs, the specific location of the emission reduction may be important. For example, the reduction of the transport of sediment in a watershed that has many man-made water impoundments, such as dams, may be of more value than the reduction of sediment transport into an unregulated and uncontrolled watershed.

One of the key provisions of many national strategies to limit the rate of growth in the amounts of atmospheric greenhouse gases is the concept of emissions trading. Emissions trading is a process whereby specific target emission rates of certain greenhouse gases are set for specific industries. A member of the industry who achieves measured emissions below the target rates may trade the difference on the open market to another who exceeds, or forecasts that it will exceed, its own emission targets. An entity responsible for measured emissions above its target rates may be subject to fines or other sanctions. The objective is to reduce the overall emission of greenhouse gases in the atmosphere, even if the emissions of one particular source are not decreased, or indeed are increased. In the last decade, the effectiveness of this market-based emissions reduction approach as applied to criteria air pollutants in the US has been demonstrated. Fledgling attempts to develop similar systems for water pollution trades and for other remediation issues are in progress, however they have been hindered by a key factor addressed by the method described herein.

The unit of measure of tradable carbon emissions that has been generally accepted is commonly known as the Carbon Emission Reduction Credit, or CERC, which is equivalent to one metric ton of carbon dioxide gas (or other greenhouse gas equivalent) that is not emitted into the earth's atmosphere (emission reduction) or one metric ton of carbon dioxide that is removed from the atmosphere (emission offset) due to a human-caused change. That is, a CERC can be generated for human activities that have occurred since a base year, e.g., 1990, that have resulted in a reduction of business-as-usual emissions of greenhouse gases. CERC as used herein is meant to include carbon offsets as well as carbon credits. Many different protocols exist to track carbon removal from the atmosphere via soil sequestration. Bcarbon by Carbonplan is one example. Another example is Verra Soils which is administered by Indigo. Further examples are provided in Daniel Sanchez, "Market Criteria for Carbon Farming Pathways" presented Jun. 29, 2022, at Carbon Farming Workshop by ARPA-E within the US Department of Energy Jun. 28-29, 2022, at Kansas City, MO, contents of which are incorporated by reference in its entirety.

For example, CERCs can be generated through energy efficiency gains of fossil fuel technology, substitution of biofuels for fossil fuels, or removal of greenhouse gases from industrial gas streams. CERCs also can be generated by sequestration of atmospheric carbon dioxide into land or water, e.g., by reforesting land or through implementation of agricultural practices that increase the storage of organic matter in the soil. Additionally, CERCs can be generated by capturing methane emitted from sewage lagoons and burning it into carbon dioxide since one ton of methane is equivalent to approximately 22 tons of carbon dioxide with respect to its global warming potential. Additional CERCs would be generated if the methane was used as a substitute for fossil fuels. Other EBCs can be generated through the modification of business-as-usual management practices. For example, a producer can switch from pesticide intensive management to "organic farming" practices and therefore, potentially earn water quality based EBCs.

A market is emerging for trading CERCs, EBCs and other green tags. One type of CERC trading involves an industrial consortium, where each industrial entity determines a rough estimate of the number of CERCs generated by its activity or needed from others due to its activity. If an individual entity has generated CERCs by changing its business-as-usual activity, e.g., by reducing the amounts of greenhouse gases emitted, it can trade the CERCs to others in the consortium.

There also have been entities involved specifically in CERC trading based on increasing the storage of carbon in soil. For example, in 1999 a consortium of Canadian power companies hired an insurance company to contractually obligate a group of Iowa farmers to twenty years of no-till farming. Based on general data, a broker for the power companies assumed that this land management practice would result in sufficient sequestration of carbon into the soil to generate CERCs. The power companies also purchased an insurance policy for protection against the possibility that no CERCs, or insufficient CERCs, would be generated by this arrangement. This trade was designed by the consortium of power companies to minimize the price that the farmers were paid. The difficulty and uncertainty of predicting these CERCs, obtaining indemnification or insurance, and banding together a sufficiently large number of farmers to generate a pool of potential CERCs large enough to overcome substantial baseline transactional costs and uncertainty whether the CERCs generated would meet current, pending or future regulatory requirements operated to drive up the costs incurred by the potential CERC purchasers, drive down the price paid to the producers and generally make it difficult to establish and engage in a market for CERCs by not efficiently maximizing incentives to producers and by not efficiently minimizing risks to purchasers.

In the absence of a globally accepted process to generate, quantify and standardize CERCs, especially CERCs generated or projected to be generated by carbon sequestration in land or plants, the market for such CERCs remains uncertain. This uncertainty hinders the ability of individual or groups of landowners and land managers, to efficiently generate, quantify, standardize, market and trade CERCs generated by carbon sequestration in the soil.

A need exists for an improved method of generating CERCs based on carbon sequestration in soil, particularly with increased certainty of a return on investment in nature-based solutions to encourage potential producers of CERCs, such as an individual landowner/manager or groups of landowners/managers to adopt practices that stimulate removal of $CO_2$ from the atmosphere and sequestration of the carbon in the soil using biodiverse indigenous plant material such as grasslands and prairies. Biodiversity calls for at least 2, 3, 5, 8, 10, 12, 15 or 20 different types or species of plants. The higher the number of different plants, the greater the biodiversity. In one embodiment the biodiverse biomass contains plant material from at least 2 different plants. In one embodiment the biodiverse biomass contains plant material from at least 3 different plants. In one embodiment the biodiverse biomass contains plant material from at least 5 different plants. In one embodiment the biodiverse biomass contains plant material from at least 8 different plants. In one embodiment the biodiverse biomass contains plant material from at least 10 different plants. In one embodiment the biodiverse biomass contains plant material from at least 12 different plants. In another embodiment the biodiverse biomass contains plant material from at least 15 different plants. In another embodiment the biodiverse biomass contains plant material from at least 20 different plants. In yet another embodiment, the number of different plants in an area of land increases over time. A method incorporating additional valuable products generated from the practice of nature-based solution practices offer greater certainty of return on investment and has the resulting technical effect of increased stimulation of carbon sequestration in soil plus generation of renewable valuable chemical products.

Soil plays a critical role in the carbon cycle since the majority of carbon in the atmosphere comes from biological reactions within the soil. The biological/physical carbon cycle occurs over days, weeks, months, and years and involves the absorption, conversion, and release of carbon by living organisms through photosynthesis, respiration, and decomposition. More carbon dioxide is stored in the world's soils than is circulated within the atmosphere. Soils are dynamic, open habitats that provide plants with physical support, water, nutrients, and air for growth. Soils also sustain an enormous population of microorganisms such as bacteria and fungi that recycle chemical elements, notably carbon and nitrogen, as well as sulfur compounds. The carbon and nitrogen cycles are important natural processes that involve the uptake of nutrients from soil, the return of organic matter to the soil by tissue aging and death, the decomposition of organic matter by soil microbes (during which nutrients or toxins may be cycled within the microbial community), and the release of nutrients into soil for uptake once again. These cycles are closely linked to the hydrologic cycle since water functions as the primary medium for chemical transport.

Carbon (C) enters the ecosystem primarily from the atmosphere, in the form of carbon dioxide ($CO_2$), and is taken up by plants and converted into biomass. Organic matter in the soil in the form of humus and other biomass contains about three times as much carbon as does land vegetation. Soils of arid and semiarid regions also store carbon in inorganic chemical forms, primarily as calcium carbonate ($CaCO_3$). These pools of carbon are important components of the carbon cycle because they are located near the soil surface where they are subject to erosion and decomposition. Each year, soils release 4-5 percent of their carbon to the atmosphere by the transformation of organic matter into $CO_2$ gas, a process termed soil respiration. This amount of $CO_2$ is more than 10 times larger than that currently produced from the burning of fossil fuels (coal and petroleum), but it is returned to the soil as organic matter by the production of biomass.

However, the primary example is to enhance the carbon cycle and its relationship to soil sequestration by plants and their roots biological processes at upper soil levels. Carbon compounds are important to the creation of 'topsoil' from the structureless, lifeless 'mineral soil' produced by the weathering of rocks. Some say that around 50-80% of the organic carbon that was once in the topsoil has been lost to the atmosphere over the last 150 years or so. Degraded soils have the potential to store up to five (5) times more organic carbon in their surface layers than they currently hold.

The cheapest, most efficient and most beneficial form of organic carbon for soil life is exudation from the actively growing roots of plants. The breakdown of fibrous roots becomes an important source of carbon in soils. Organic carbon additions are governed by the volume of plant roots per unit of soil and their rate of growth. The more active plant roots there are, the more carbon is added. The present method mimics the natural historical cycle of grasslands or prairies in that a biodiverse collection of plants occupy an area of land, unlike monocultures of a single crop, and the above-ground plant material is harvested three or less times in a 12-month period of time. The biodiverse collection of plants include at least 2, 3, 5, 8, 10, 12, 15 or 20 different kinds of plants, indigenous to the region. Upon harvesting of the above-ground plant material, the plant naturally operates to delivers nutrients deeper into the soil and plant roots rapidly penetrate deeper into the soil. These deeper reaching roots exude (secrete) a vast array of compounds into the rhizosphere and regulate soil microbial communities, which encourage beneficial symbioses, change the chemical and physical properties of the soil, encouraging $CO_2$ absorption by aerobic soil microbes. The ability to secrete a vast array of compounds into the rhizosphere is one of the most remarkable metabolic features of plant roots, with nearly 5% to 21% of all photosynthetically fixed carbon being transferred to the rhizosphere through root exudates according to some studies. The biogeochemical reactions induced by microorganisms at the rhizosphere soil-root interface play an important role in the bioavailability of nutrients and metals to plants. This microenvironment is characterized by distinct physical, chemical, and biological conditions compared with the bulk soil, largely created by the plant roots and its microbial associations. Such associations can include non-symbiotic and symbiotic organisms such as bacteria and mycorrhizal fungi. These microbial populations are an essential part of the rhizosphere and affect the rhizosphere soil by their various activities such as water and nutrient uptake, exudation, and biological transformations.

The biodiverse nature of the plant material and the restricted harvesting of the above-ground plant material stimulates transporting organic acids, sugars, amino acids, lipids, coumarins, flavonoids, proteins, enzymes, aliphatics, metals, and aromatics within this microzone. The organic acids provide substrates for microbial metabolism and serve as intermediates for biogeochemical reactions in soil. Nutrients and metals are typically present in the soil solution at low concentrations and tend to form sparingly soluble minerals (except nitrogen, sulfur, and boron), or may be adsorbed to a solid phase through ion exchange, hydrogen bonding, or complexation. The extent to which they are transferred from the soil to the biota (i.e., microbes or plants) is dependent on the biogeochemical interactions and/or processes among the soil, plant roots, and microorganisms in the rhizosphere. At this interface, the presence of root exudates may influence chemical reaction kinetics within the soil environment and subsequently affect biological activities. As such, the role of the rhizosphere on biogeochemical processes within the soil is essential for developing bioremediation technologies of inorganic and organic contaminants In this positive feedback loop, $CO_2$ respired by plant roots and aerobic soil microbes, slowly moves upwards through the topsoil and increases the partial pressure of $CO_2$ beneath the crop/pasture canopy, enhancing photosynthetic potential. The regenerative regimes restore soil carbon and soil life. Carbon sequestration in soil is the most potent mechanism available for reducing greenhouse gases and mitigating climate change. In addition to root exudation, soil carbon levels can also be increased using principles employed in the rapidly expanding arena of ecological agriculture, which includes biodynamic, organic and biological farming used in association with the present irrigation method. There are many and varied practices including the use of cover crops, green manures, mulches, worm juice, fish and seaweed products, animal manures, recycled green waste, biosolids, composts, compost teas, liquid injection, humic substances, microbial stimulants and innumerable combinations thereof.

Organic carbon moves between various 'pools' in the soil, some of which are short lived while others may persist for thousands of years. Glomalin and humic substances are two of the relatively stable forms of soil carbon. Their creation and destruction are strongly influenced by land management.

Glomalin is a glycoprotein produced by arbuscular mycorrhizal fungi living on plant roots. Most current soil chemical extraction techniques greatly underestimate the amount of glomalin, which can persist for several decades and may account for one third of the organic carbon stored in agricultural soils. Dr Sara Wright (USDA-ARS) has shown that glomalin contributes about seven times more carbon to total soil organic carbon than do humic acids. This discovery has attracted a great deal of interest from a carbon storage and carbon trading perspective, in addition to the multiple benefits for soil and catchment health. Glomalin forms on the outer surface of the hyphae of mycorrhizal fungi, which colonize on the roots of certain plants. The number and activity of these affects the amount of glomalin that can be produced. Most members of the grass family are excellent host mycorrhizal fungi, which have up to 100 meters of microscopic fungi per gram of soil under healthy grassland conditions. Enhancing grassland root production with the present method thus enhances glomalin production.

Humus use is the best known of the stable organic fractions in soils and can also be stimulated by the present method. Humus has never been clearly defined or understood. One reason for this is that humus is an integral component of the soil matrix and cannot be successfully isolated for scientific research. Synthetic humus or extracted humus does not have the same properties as humus found naturally within the soil. There are many theories on the formation of humus, most of which suggest a microbial resynthesis and polymerization of carbon compounds derived from organic matter. If soil conditions are conducive to biological activity however, levels of humus can increase to a greater extent than would be possible from the weight of organic materials grown or applied. This suggests that microbial stimulation per se may be the factor of greatest importance, with organic matter simply fueling the process.

In healthy soils, stable humic substances can persist for over one thousand years. Bare earth and practices that destroy soil structure, such as intensive tillage or the application of anhydrous ammonia result in the loss of humus. Humic substances have significance above and beyond the relatively long-term sequestration of atmospheric carbon. They are extremely important in terms of pH buffering, inactivation of pesticides and other pollutants, improved plant nutrition and increased water-holding capacity of soil. Humic substances can also effectively ameliorate the symptoms of dryland salinity by chelating salts and stimulating biological activity. Loss of humus therefore has a highly significant effect on the health and productivity of soil.

By increasing soil carbon absorption by the present method, significant increases in net carbon credits result. The world's soils hold around twice as much carbon as the atmosphere and almost three times as much carbon as the vegetation. Soil represents the largest carbon sink over which we have control. Improvements in soil carbon levels could be made in all rural areas, whereas the regions suited to carbon sequestration in plantation timber are limited.

As discussed, a need exists for an improved method of stimulating the sequestration of carbon in the soil, generating environmental benefit credits (EBCs) and CERCS, and producing a profitable valuable chemical product or fuel.

Systems and methods in accordance with the present disclosure can be used to integrate gas fermentation with land management techniques which harvests or generates carbon-based biodiverse biomass, in a way that stimulates sequestration of carbon in the soil. Integrating a gas fermentation (hereinafter referred to as "GF") process allows for the conversion of biodiverse biomass into valuable chemical products and or fuel while also generating CERCS for sequestering carbon in the soil. Gas fermentation systems may be co-located with the source of biodiverse biomass or may be co-located with a supplemental source of carbon. It is also envisioned that the gas fermentation system may be co-located with a facility accepting and using the chemical product or fuel.

Exemplary harvesting of biodiverse biomass include harvesting biomass from grasslands, harvesting biomass from prairies, harvesting biomass from coastal areas including mangrove forests and swamp forests, harvesting biomass from forests. Harvesting biomass from degraded or blighted land has the advantage of rehabilitating the land over an extended period of time, commonly about 10 years. Harvesting biomass includes cutting or mowing overgrown flora and grasses and collecting fallen or discarded wooded plants or trees. As discussed, harvesting biomass as a way to stimulate deeply-rooted perennial grass growth and soil carbon sequestration. Other sources of harvested biomass include native North American prairie grasses such as switch grass and bred versions of other grasses such as *Miscantheus giganteus*, sawdust, waste wood, leaves, vegetables, nut shells, straw, cotton trash, rice hulls, and orange peels. Biomass harvesting produced by the cultivation of micro and macroalga. Animal waste including poultry litter, dairy manure, and other manures. Some commercial byproducts are also suitable feedstock including paper sludge, distiller's grain, sewage sludge, and municipal solid waste. The harvesting process further stimulates the fixation of excess atmospheric carbon into the new growth biomass and the further sequestration of carbon from the soil.

The term "nature-based solutions" as defined by the European Commission as "solutions that are inspired and supported by nature, which are cost-effective, simultaneously provide environmental, social and economic benefits and help build resilience. Such solutions bring more, and more diverse, nature and natural features and processes into cities, landscapes and seascapes, through locally adapted, resource-efficient and systemic interventions." Other organizations and governments use related terms, such as green infrastructure, natural infrastructure, natural and nature-based features.

Exemplary nature-based solutions include the use of algae and wetlands to treat sewage, as done in the East Kolkata wetlands in West Bengal of India. Another example would be the restoration and/or protection of mangroves along coastlines. Mangroves moderate the impact of waves and wind on coastal settlements or cities and sequester CO2. Mangroves also provide nursery zones for marine life that can be the basis for sustaining fisheries on which local populations may depend. Additionally, mangrove forests can help to control coastal erosion resulting from sea level rise. Other examples include green roofs or green walls to moderate the impact of high temperatures, capture storm water, abate pollution, and act as carbon sinks, while simultaneously enhancing biodiversity.

After the biodiverse biomass is harvested and collected, the material may be stored until needed for feedstock. After storage, the biomass is transported to the processing facility comprising the anerobic digestor, the methane conversion system and the gas fermentation system. Examples of modes of transport include rail, or truck and trailers. The harvested biodiverse biomass is anaerobically digested to product a stream comprising methane. The anerobic digestion may be conducted by any known anerobic digestion techniques, of which there are many. The anerobic digestion results in the breaking down of the biodiverse plant matter by microbial action is the absence of air to produce a gas with high methane content. A typical anaerobic digestion unit may include a digestor tank with ancillary equipment such as a generator or biogas storage tank, pipework, and perhaps a flare stack, although it is envisioned that flare gasses may be passed to the methane conversion unit and or the gas fermentation system. Anerobic digestion may further generate solids which are useful as soil amendments. The solids may be sold as product for soil amendments, or may be used by the operator for soil amendments.

As the harvesting of the biodiverse biomass may yield a varying amount of biodiverse biomass with respect to time, a supplemental source of carbon may be additional used as feedstock. The supplemental source may be another bio-derived source so that the chemical product or fuel comprises little or no fossil carbon, and 99 mass-% or more of modern carbon as defined by ASTM Method D6866. Animal manure is a desirable supplemental bio-derived material and is commonly subjected to anerobic digestion. Suitable examples of supplemental bio-derived material is animal waste, agricultural waste, forestry waste, sewage, food waste, brewery grain byproducts, organic industry waste, seaweed, plankton, algae, fish, fish waste, potato waste, sugar cane waste, sugar beet waste, straw, paper waste, manure, sawdust, wood, leaves, vegetables, nut shells, cotton trash, rice hulls, orange peels, poultry lotter, dairy manure, paper sludge, sewage sludge, sawdust, wood, leaves, vegetables, nut shells, straw, cotton trash, rice hulls, orange peels, poultry litter, dairy manure, other manures, paper sludge, distillers grain, residential compost, industrial compost and sewage sludge. The ratio of biodiverse biomass and supplemental carbon source may vary with time as the amount of biodiverse biomass may be high near to the time of harvest, and lower as a subject time for harvesting approaches. To maintain a steady feed to the anerobic digestion system, and subsequent downstream systems, the supplemental carbon source may vary depending upon the available biodiverse biomass. Alternatively, buffer or storage tanks may be used at different points of the overall process flow scheme.

In one embodiment the supplemental C1 carbon source may be already in the form of a gas, or a solid or liquid material (e.g., solid or liquid waste) may be first processed in a preliminary step of the overall gas fermentation process to generate synthesis gas known as syngas which in turn is provided to the bioreactor of the gas fermentation system. The preliminary step to generate syngas may involve, reforming, partial oxidation, plasma, or gasification processes. Examples of gasification processes include gasification of coal, gasification of refinery residues, gasification of petroleum coke, gasification of biomass, gasification of lignocellulosic material, gasification of waste wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of landfill gas, gasification of biogas such as when biogas is added to enhance gasification of another material. Examples of reforming processes include, steam methane reforming, steam naphtha reforming, reforming of natural gas, reforming of biogas, reforming of landfill gas, reforming of coke oven gas, reforming of pyrolysis off-gas, reforming of ethylene production off-gas, naphtha reforming, and dry methane reforming. Examples of partial oxidation processes include thermal and catalytic partial oxidation processes, catalytic partial oxidation of natural gas, partial oxidation of hydrocarbons, partial oxidation of biogas, partial oxidation of landfill gas, or partial oxidation of pyrolysis off-gas. Examples of municipal solid waste include tires, plastics, refuse derived fuel, and fibers such as in shoes, apparel, and textiles. Municipal solid waste may be simply landfill-type waste and may be sorted or unsorted. Examples of biomass may include lignocellulosic material and microbial biomass. Lignocellulosic material may include agriculture waste and forest waste. Further examples of useful biomass include woody biomass. Examples include woody biomass from sustainable forest management practices, above ground biomass harvested from prairie and grassland rehabilitation and soil carbon stimulation, waste biomass produced by regenerative farming practices, biomass derived from sustainable harvesting during coastal system rehabilitation, macroalga cultivation and harvest.

The substrate and/or C1-carbon source may be a gas stream comprising methane. Such a methane containing gas may be obtained from: fossil methane emissions such as during fracking, wastewater treatment, livestock, agriculture, and municipal solid waste landfills. It is also envisioned that the methane may be burned to produce electricity or heat and the C1 by-products may be used as the substrate or carbon source.

Methane is generated in the anerobic digestion system and an effluent comprising methane is withdrawn and passed to a methane conversion unit. Often, a stream comprising oxygen is also passed to the methane conversion unit. The effluent comprising methane may be biogas. The methane conversion unit may be a biogas reformer. Hydrogen may be produced by the biogas reformer. Other suitable methane conversion units include a methane steam reforming unit, a partial oxidation unit, an auto thermal reforming unit, an oxidation unit, a combustion unit, a biogas reforming unit, or a gasification unit. The methane conversion unit produced a stream comprising syngas. An effluent of the methane conversion unit comprises $CO_2$, CO and $H_2$. The effluent is passed to a microbial gas fermentation system comprising at least one C1 fixing microorganism and a nutrient solution in at least one bioreactor.

The microorganism of the disclosure may be cultured with the gaseous substrate to produce one or more sustainable carbon products with a low carbon footprint and relatively low impact on the climate. For instance, the microorganism of the disclosure may produce or may be engineered to produce ethanol, acetate, 1-butanol, 2,3-butanediol, lactate, butene, butadiene, methyl ethyl ketone (2-butanone), ethylene, acetone, isopropanol, lipids, 3-hydroxypropionate (3-HP), terpenes, including isoprene, fatty acids, 2-butanol, 1,2-propanediol, 1 propanol, 1 hexanol, 1 octanol, chorismate-derived products, 3 hydroxybutyrate, 1,3 butanediol, 2-hydroxyisobutyrate or 2-hydroxyisobutyric acid, isobutylene, adipic acid, 1,3 hexanediol, 3-methyl-2-butanol, 2-buten-1-ol, isovalerate, isoamyl alcohol, and/or monoethylene glycol in addition to ethylene. In certain embodiments, microbial biomass itself may be considered a product.

Often, the focus of nature-based solutions is on benefits such as enhanced biodiversity and aiding those with lower socio-economic statuses. In addition to these, many nature-based solutions produce biomass that can be utilized as feedstocks for gas fermentation processes. Harvesting such biomass at maximum intervals of time further stimulated the sequestration of carbon in the soil.

Ethanol and Derivatives

In one embodiment, ethanol or ethyl alcohol produced according to the method of the disclosure may be used in numerous product applications, including antiseptic hand rubs (WO 2014/100851), therapeutic treatments for methylene glycol and methanol poisoning (WO 2006/088491), as a pharmaceutical solvent for applications such as pain medication (WO 2011/034887) and oral hygiene products (U.S. Pat. No. 6,811,769), as well as an antimicrobial preservative (U.S. Patent Application No. 2013/0230609), engine fuel (U.S. Pat. No. 1,128,549), rocket fuel (U.S. Pat. No. 3,020,708), plastics, fuel cells (U.S. Pat. No. 2,405,986), home fireplace fuels (U.S. Pat. No. 4,692,168), as an industrial chemical precursor (U.S. Pat. No. 3,102,875), *Cannabis* solvent (WO 2015/073854), as a winterization extraction solvent (WO 2017/161387), as a paint masking product (WO 1992/008555), as a paint or tincture (U.S. Pat. No. 1,408,091), purification and extraction of DNA and RNA (WO 1997/010331), and as a cooling bath for various chemical reactions (U.S. Pat. No. 2,099,090). In addition to the foregoing, the ethanol generated by the disclosed method may be used in any other application for which ethanol might otherwise be applicable.

A further embodiment comprises converting the ethanol generated by the method into ethylene. This can be accomplished by way of an acid catalyzed dehydration of ethanol to give ethylene according to the following formula:

$$CH_3CH_2OH \rightarrow CH_2=CH_2+H_2O$$

The ethylene generated in this way may be used for a variety of applications on its own or can be used as a raw material for more refined chemical products. Specifically, ethylene alone may be used as an anesthetic, as part of a mixture with nitrogen to control ripening of fruit, as a fertilizer, as an element in the production of safety glass, as part of an oxy-fuel gas in metal cutting, welding and high velocity thermal spraying, and as a refrigerant.

As a raw material, ethylene can used in the manufacture of polymers such as polyethylene (PE), polyethylene terephthalate (PET) and polyvinyl chloride (PVC) as well as fibres and other organic chemicals. These products are used in a wide variety of industrial and consumer markets such as the packaging, transportation, electrical/electronic, textile and construction industries as well as consumer chemicals, coatings and adhesives.

Ethylene can be chlorinated to ethylene dichloride (EDC) and can then be cracked to make vinyl chloride monomer (VCM). Nearly all VCM is used to make polyvinyl chloride which has its main applications in the construction industry.

Other ethylene derivatives include alpha olefins which are used in Linear low-density polyethylene (LLDPE) production, detergent alcohols and plasticizer alcohols; vinyl acetate monomer (VAM) which is used in adhesives, paints, paper coatings and barrier resins; and industrial ethanol which is used as a solvent or in the manufacture of chemical intermediates such as ethyl acetate and ethyl acrylate.

Ethylene may further be used as a monomer base for the production of various polyethylene oligomers by way of coordination polymerization using metal chloride or metal oxide catalysts. The most common catalysts consist of titanium (III) chloride, the so-called Ziegler-Natta catalysts. Another common catalyst is the Phillips catalyst, prepared by depositing chromium (VI) oxide on silica.

Polyethylene oligomers so produced may be classified according to its density and branching. Further, mechanical properties depend significantly on variables such as the extent and type of branching, the crystal structure, and the molecular weight. There are several types of polyethylene which may be generated from ethylene, including, but not limited to:

Ultra-high-molecular-weight polyethylene (UHMWPE);
Ultra-low-molecular-weight polyethylene (ULMWPE or PE-WAX);
High-molecular-weight polyethylene (HMWPE);
High-density polyethylene (HDPE);
High-density cross-linked polyethylene (HDXLPE);
Cross-linked polyethylene (PEX or XLPE);
Medium-density polyethylene (MDPE);
Linear low-density polyethylene (LLDPE);
Low-density polyethylene (LDPE);
Very-low-density polyethylene (VLDPE); and
Chlorinated polyethylene (CPE).

Low density polyethylene (LDPE) and linear low-density polyethylene (LLDPE) mainly go into film applications such as food and non-food packaging, shrink and stretch film, and non-packaging uses. High density polyethylene (HDPE) is used primarily in blow molding and injection molding applications such as containers, drums, household goods, caps and pallets. HDPE can also be extruded into pipes for water, gas and irrigation, and film for refuse sacks, carrier bags and industrial lining.

According to one embodiment, the ethylene formed from the ethanol described above may be converted to ethylene oxide via direct oxidation according to the following formula:

$$C_2H_4+O_2 \rightarrow C_2H_4O$$

The ethylene oxide produced thereby is a key chemical intermediate in a number of commercially important processes including the manufacture of monoethylene glycol. Other EO derivatives include ethoxylates (for use in shampoo, kitchen cleaners, etc.), glycol ethers (solvents, fuels, etc.) and ethanolamines (surfactants, personal care products, etc.).

Monoethylene Glycol and Derivatives

According to one embodiment of the disclosure, the ethylene oxide produced as described above may be used to produce commercial quantities of monoethylene glycol by way of the formula:

$$(CH_2CH_2)O+H_2O \rightarrow HOCH_2CH_2OH$$

According to another embodiment, the claimed microorganism can be modified in order to directly produce monoethylene glycol. As described in WO 2019/126400, the disclosure of which is incorporated by reference herein, the microorganism further comprises one or more of an enzymes capable of converting acetyl-CoA to pyruvate; an enzyme capable of converting pyruvate to oxaloacetate; an enzyme capable of converting pyruvate to malate; an enzyme capable of converting pyruvate to phosphoenolpyruvate; an enzyme capable of converting oxaloacetate to citryl-CoA; an enzyme capable of converting citryl-CoA to citrate; an enzyme capable of converting citrate to aconitate and aconitate to iso-citrate; an enzyme capable of converting phosphoenolpyruvate to oxaloacetate; an enzyme capable of converting phosphoenolpyruvate to 2-phospho-D-glycerate; an enzyme capable of converting 2-phospho-D-glycerate to 3-phospho-D-glycerate; an enzyme capable of converting 3-phospho-D-glycerate to 3-phosphonooxypyruvate; an enzyme capable of converting 3-phosphonooxypyruvate to 3-phospho-L-serine; an enzyme capable of converting 3-phospho-L-serine to serine; an enzyme capable of converting serine to glycine; an enzyme capable of converting 5,10-methylenetetrahydrofolate to glycine; an enzyme capable of converting serine to hydroxypyruvate; an enzyme capable of converting D-glycerate to hydroxypyruvate; an enzyme capable of converting malate to glyoxylate; an enzyme capable of converting glyoxylate to glycolate; an enzyme capable of converting hydroxypyruvate to glycolaldehyde; and/or an enzyme capable of converting glycolaldehyde to ethylene glycol.

Monoethylene glycol produced according to either of the described methods may be used as a component of a variety of products including as a raw material to make polyester fibers for textile applications, including nonwovens, cover stock for diapers, building materials, construction materials, mad-building fabrics, filters, fiberfill, felts, transportation upholstery, paper and tape reinforcement, tents, rope and cordage, sails, fish netting, seatbelts, laundry bags, synthetic artery replacements, carpets, rugs, apparel, sheets and pillowcases, towels, curtains, draperies, bed ticking, and blankets.

MEG may be used on its own as a liquid coolant, antifreeze, preservative, dehydrating agent, drilling fluid or any combination thereof. The MEG produced may also be used to produce secondary products such as polyester resins for use in insulation materials, polyester film, de-icing fluids, heat transfer fluids, automotive antifreeze and other liquid coolants, preservatives, dehydrating agents, drilling fluids, water-based adhesives, latex paints and asphalt emulsions, electrolytic capacitors, paper, and synthetic leather.

Importantly, the monoethylene glycol produced may be converted to the polyester resin polyethylene terephthalate ("PET") according to one of two major processes. The first process comprises transesterification of the monoethylene glycol utilizing dimethyl terephthalate, according to the following two-step process:

First Step

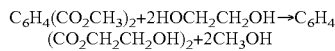

Second Step

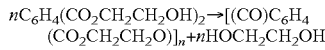

Alternatively, the monoethylene glycol can be the subject of an esterification reaction utilizing terephthalic acid according to the following reaction:

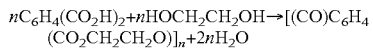

The polyethylene terephthalate produced according to either the transesterification or esterification of monoethylene glycol has significant applicability to numerous packaging applications such as jars and, in particular, in the production of bottles, including plastic bottles. It can also be used in the production of high-strength textile fibers such as Dacron, as part of durable-press blends with other fibers such as rayon, wool, and cotton, for fiber fillings used in insulated clothing, furniture, and pillows, in artificial silk, as carpet fiber, automobile tire yarns, conveyor belts and drive belts, reinforcement for fire and garden hoses, seat belts, nonwoven fabrics for stabilizing drainage ditches, culverts, and railroad beds, and nonwovens for use as diaper topsheets, and disposable medical garments.

At a higher molecular weight, PET can be made into a high-strength plastic that can be shaped by all the common methods employed with other thermoplastics. Magnetic recording tape and photographic film are produced by extrusion of PET film. Molten PET can be blow-molded into transparent containers of high strength and rigidity that are also virtually impermeable to gas and liquid. In this form, PET has become widely used in bottles, especially plastic bottles, and in jars.

Isopropanol and Derivatives

In an additional embodiment, isopropanol or isopropyl alcohol (IPA) produced according to the method may be used in numerous product applications, including either in isolation or as a feedstock for the production for more complex products. Isopropanol may also be used in solvents for cosmetics and personal care products, de-icers, paints and resins, food, inks, adhesives, and pharmaceuticals, including products such as medicinal tablets as well as disinfectants, sterilizers, and skin creams.

The IPA produced may be used in the extraction and purification of natural products such as vegetable and animal oil and fats. Other applications include its use as a cleaning and drying agent in the manufacture of electronic parts and metals, and as an aerosol solvent in medical and veterinary products. It can also be used as a coolant in beer manufacture, a coupling agent, a polymerization modifier, a de-icing agent and a preservative.

Alternatively, the IPA produced according to the method of the disclosure may be used to manufacture additional useful compounds, including plastics, derivative ketones such as methyl isobutyl ketone (MIBK), isopropylamines and isopropyl esters. Still further, the IPA may be converted to propylene according to the following formula:

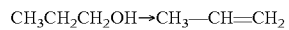

The propylene produced may be used as a monomer base for the production of various polypropylene oligomers by way of chain-growth polymerization via either gas-phase or bulk reactor systems. The most common catalysts consist of titanium (III) chloride, the so-called Ziegler-Natta catalysts and metallocene catalysts.

Polypropylene oligomers so produced may be classified according to tacticity and can be formed into numerous products by either extrusion or molding of polypropylene pellets, including piping products, heat-resistant articles such as kettles and food containers, disposable bottles (including plastic bottles), clear bags, flooring such as rugs and mats, ropes, adhesive stickers, as well as foam polypropylene which can be used in building materials. Polypropylene may also be used for hydrophilic clothing and medical dressings.

Commodity Chemicals and Articles

According to one embodiment, the gas fermentation product is a commodity chemical. In another embodiment, the gas fermentation product is a commodity chemical, where the commodity chemical is catalytically converted, for example, by catalytically upgrading, into molecules, or one or more second products, wherein the one or more second products are integrated into existing or newly built infrastructure or feedstock and product transportation networks.

In one embodiment, wherein the commodity chemical is selected from ethanol, isopropanol, monoethylene glycol, sulfuric acid, propylene, sodium hydroxide, sodium carbonate, ammonia, benzene, acetic acid, ethylene, ethylene oxide, formaldehyde, methanol, or any combination thereof. In one embodiment, the commodity chemical is aluminum sulfate, ammonia, ammonium nitrate, ammonium sulfate, carbon black, chlorine, diammonium phosphate, monoammonium phosphate, hydrochloric acid, hydrogen fluoride, hydrogen peroxide, nitric acid, oxygen, phosphoric acid, sodium silicate, titanium dioxide, or any combination thereof. In another embodiment, the commodity chemical is acetic acid, acetone, acrylic acid, acrylonitrile, adipic acid, benzene, butadiene, butanol, caprolactam, cumene, cyclohexane, dioctyl phthalate, ethylene glycol, methanol, octanol, phenol, phthalic anhydride, polypropylene, polystyrene, polyvinyl chloride, polypropylene glycol, propylene oxide, styrene, terephthalic acid, toluene, toluene diisocyanate, urea, vinyl chloride, xylenes, or any combination thereof.

Secondary Products

The disclosed systems and methods are also suitable for providing one or more secondary products that are independent of the gas fermentation product (e.g., ethylene, ethanol, acetate, etc.). For example, in certain embodiments, microbial biomass itself may be considered a secondary product. In such embodiments, biomass from a bioreactor, such as dead microorganisms, may be used as a carbon source for further fermentation by gasifying the biomass. Additionally, or alternatively, microbial proteins or other biomass may be recovered from a bioreactor and sold/used separately from the primary product (e.g., ethylene, ethanol, acetate, 1-butanol, etc.) as a supplement, such as a nutritional supplement and/or an animal feed. Known methods for using such biomass as a nutritional supplement or animal feed are disclosed in U.S. Pat. No. 10,856,560, which is herein incorporated by reference.

Additionally, or alternatively, biochar may be a secondary product. In embodiments that involve or comprise gasification of solid or liquid carbonaceous materials to produce a feedstock, biochar can be incidentally produced. Biochar is carbon rich and highly structured, and therefore it can be useful as, for example, fertilizer, among other applications.

Additionally, or alternatively, unutilized carbon dioxide, which may be in the form of an off-gas from the gas fermentation, may be a secondary product. Such unutilized carbon dioxide will be in a stoichiometrically higher proportion in the off-gas compared to the feedstock, and this relative purity can make the carbon dioxide useful. For example, the unutilized carbon can be sequestered by an operator for the purposes of obtaining carbon credits, or it may be combined with hydrogen gas ($H_2$), such as "green hydrogen" resulting from electrolysis, and recycled back into the gas fermenter or bioreactor as feedstock.

Exemplary refining or chemical processes that may utilize the product of the gas fermentation process include distillation, including as examples, at atmospheric pressure, at reduced pressure, stripping, rerunning, stabilization, super fractionation, azeotropic, extractive, or any combination thereof; thermal cracking including for example, Visabreaking, coking, delayed coking, fluid coking, coke gasification, Flexicoking™ process, Aquaconversion™ process, Asphalt Coking Technology Process (ASCOT) Process, Cherry-P Process, Continuous Coking Process, Decarbonizing Process, ET-II Process, Eureka Process, FTC Process, HSC Process, Mixed-Phase Cracking Process, Shell Thermal Cracking Process, Tervahl-T Process, or any combination thereof; catalytic cracking as exemplified by fixed bed, moving bed, fluid bed, coke formation, Asphalt Residual Treating (ART) Process, Residue Fluid Catalyst Cracking Process, Heavy Oil Treating Process, R2R Process, Reduced Crude Oil Conversion Process, Shell FCC Process, and S&W Fluid Catalytic Cracking Process, or any combination thereof; hydrotreating as exemplified by hydrodesulfurization in downflow fixed-bed, upflow expanded-bed, distillate hydrodesulfurization, heavy feedstock hydrodesulfurization, Resid Desulfurization Process, Vacuum Resid Desulfurization Process, Residfining Process; biodesulfurization, or any combination thereof; hydrocracking as exemplified by Aquaconversion Process, Asphaltenic Bottom Cracking Process, CANMET Process, Chevron RDS Isomax Process, Chevron VRDS Process, ENI Slurry-Phase Technology, Gulf Resid Hydrodesulfurization Process, H-G Hdrocracking Process, H-Oil Process, HYCAR Process, Hyvahl-F Process, IFP Hydrocracking Process, Isocracking Process, LC-Fining Process, MAKfining Process, Microcat-RC Process, Mild Hydrocracking Process, MRH Process, RCD Unibon Process, Residfining Process, Residue Hydroconversion Process, Shell Residual Oil Process, Tervahl-H Process, Unicracking Process, Uniflex Process, Veba Combi Cracking Process, or any combination thereof; solvent processes as exemplified by desphalting processes, Deep Solvent Deasphalting Process, Demex Process, MDS Process, Residuum Process, Solvahl Process, Lube Deasphalting, dewaxing processes, Cold Press Process, Solvent Dewaxing Process, Urea Dewaxing Process, Centrifuge Dewaxing Process, Catalytic Dewaxing Process, dewaxing heavy feedstocks, or any combination thereof; product improvement processes including reforming, isomerization, hydroisomerization, alkylation, polymerization, treating, acid processes, clay processes, oxidative processes solvent processes, or any combination thereof; gasification processes including primary gasification, secondary gasification, water-gas shift reactions, carbon dioxide gasification, hydrogasification, methanation, Fischer-Tropsch synthesis, gasification of residua and residua, gasification of residua with biomass, gasification of residua with waste, or any combination thereof; hydrogen production and hydrogen purification; gas cleaning processes as exemplified by enrichment, water removal including, for example, adsorption and membrane, liquid removal including, for example, extraction, absorption and fractionation, nitrogen removal, acid gas removal, fractionation, and Clause Process.

Examples of reforming processes include thermal reforming, catalytic reforming in fixed bed mode and in moving bed mode, and fluid bed reforming. Examples of isomerization processes include Butamer Process, Butomerate Process, Hysomar Process, Iso-Kel Process, Isomate Process, Isomerate Process, Penex Process, and Pentafining Process. Examples of alkylation processes include sulfuric acid alkylation and hydrofluoric alkylation. Examples of polymerization processes include thermal, solidphosporic acid, and bulk acid. Examples of caustic treating processes include Dualayer Distillate Process, Dualayer Gasoline Process, Electrolytic Mercaptan Process, Ferrocyanide Process, Lye Treatment, Mercapsol Process, Polysulfide Process, Sodasol Process, Solutizer Process, Steam-Regenerative Caustic Treatment, and Unisol Process. Examples of acid treating processes include Nalfining Process, and Sulfuric Acid Treatment. Example of Clay treating processes include Alkylation Effluent Treatment, Arosorb Process, bauxite treatment, continuous contact filtration process, cyclic adsorption process, gray clay treatment, percolation filtration process, and Thermofor Continuous Percolation Process. Examples of oxidative treatment processed include Bender Process, Copper Sweetening Process, Doctor Process, Hypochlorine Sweetening Process, Inhibitor Sweetening Process, and Merox Process.

Refining processes listed are known and described in Speight, James G. Handbook of Petroleum Refining. Taylor & Francis, 2017.

Products made or resulting from any of the above chemical processes may include, but are not limited to, a commodity chemical selected from ethanol, isopropanol, monoethylene glycol, sulfuric acid, propylene, sodium hydroxide, sodium carbonate, ammonia, benzene, acetic acid, ethylene, ethylene oxide, formaldehyde, methanol, or any combination thereof. In another embodiment, the commodity chemical is incorporated into one or more articles, converted into one or more second products, or any combination thereof. In one embodiment, the one or more articles, the one or more second products, or any combination thereof, are selected from acetate, 1-butanol, butyrate, 2,3-butanediol, lactate, butene, butadiene, methyl ethyl ketone, acetone, lipids, 3-hydroxyproprionate, terpenes, isoprene, fatty acids, 2-butanol, 1,2-propanediol, 1 propanol, 1 hexanol, 1 octanol, chorismite-derived products, 3-hydroxybutyrate, 1,3-butanediol, 2-hydroxyisobutyrate, 2-hydroxyisobutyric acid, isobutylene, adipic acid, keto-adipic acid, 1,3-hexanediol, 3-methyl-2-butanol, 2-buten-1-ol, isovalerate, isoamyl alcohol, or any combination thereof.

The products of gas fermentation can be catalytically converted, for example, by a catalytic process unit. Additionally, or alternatively, the products of gas fermentation can be catalytically converted, for example, by catalytically upgrading, into molecules, or one or more second products, wherein the one or more second products are integrated into existing or newly built infrastructure or feedstock and product transportation networks. Thus, in some embodiments, molecules produced via the catalysis of the products of gas fermentation processes may also be considered desirable products or further products of fermentation. For example, in a gas fermentation system that produces ethanol, that ethanol can reacted into a range of molecules, such as propane and BTEX, and these propane and BTEX molecules can be directly introduced into the feedstock or transported via a new or existing pipeline to a refinery/chemical plant.

A catalytic process unit can be a device consisting of one or more vessels and/or towers or piping arrangements, which includes the continuous stirred tank reactor (CSTR), immobilized cell reactor (ICR), trickle bed reactor (TBR), bubble column, gas lift fermenter, membrane reactor such as hollow fiber membrane bioreactor (HFMBR), static mixer, or other vessel or other device suitable for gas-liquid contact, fixed bed, moving bed, simulated moving bed, fluidized bed, entrained bed, slurry reactor, packed bed, trickle bed, batch, semi batch, continuous, plug flow, flash, dense phase, fixed bed, downflow fixed bed, upflow expanded bed, and ebullating bed.

The types of catalysts used in the catalytic process unit can include, but are not limited to, natural clays, supported or unsupported metal or metal oxide containing catalysts, acid catalysts, zeolites, organometallic compounds. Examples include activated natural or synthetic material including activated, such as acid treated, natural clays such as bentonite type of synthesized silica-alumina or silica-magnesia, optionally with added oxides of zirconium, boron or thorium; mixed metal oxides supported on alumina or silica, such as tungsten-nickel sulfide or cobalt; metal and mixed metals containing catalysts such as platinum, palladium, rhenium, rhodium, copper, nickel, optionally supported on a silica or silica-alumina base; aluminum chloride, hydrogen chloride, sulfuric acid, hydrogen fluoride, phosphates, liquid phosphoric acid, phosphoric acid on kieselguhr, copper pyrophosphate pellets, phosphoric acid film on quarts, aluminosilicates, iron, vanadium, vanadium oxide on silica, nickel, silicone dioxide, carbonic anhydrase, iodine, zeolites, silver on alumina, Ziegler-natta catalysts, organometallic compounds, iron oxide stabilized by chromium oxide, copper, copper-zinc-alumina, promoted iron where the promoters can be potassium oxide, aluminum oxide, and calcium oxide, and iron-chrome.

Referring now to FIG. 1, which illustrates an integration of a GF system 114 and a natural climate solution (or nature-based solution) 100 which may be a specific harvesting regime for above-ground biodiverse plant material. Examples of harvesting techniques include cutting or mowing or grazing. An optional downstream processing system 118 which can convert the product of the gas fermentation process to another product or article 120. The optional downstream processing system may be a chemical processing facility or an oil refining facility. The feedstock to the anaerobic digestion process 104 is a carbon source 102 that results from harvesting a biodiverse biomass source such as above ground plant material from an area of biodiverse grasslands or prairies lands and was transported to an anaerobic digestion process 104 as an input or feed. In an embodiment, the process begins with the introduction of carbon source into anerobic digestion process 104. Supplemental bioderived material is also optionally introduced to anerobic digestion process 106 or is mixed with biodiverse biomass 102 before being introduced to anerobic digestion process 104. Anaerobic digestion process 104 proceeds according to known anaerobic digestion techniques to produce effluent stream 108 comprising methane.

In another embodiment, the method involves harvesting a biodiverse biomass of above-ground plant material comprising at least about 2, 3, 5, 8, 10, 12, 15 or 20 different species of plants from an area of land wherein the harvesting is conducted no more than one, two, or three times in a 12-month period of time, 100. The method ends with providing the harvested biodiverse biomass of above-ground plant material to a system comprising an anerobic digestion zone, a methane conversion zone and a gas fermentation zone.

Effluent stream 108 comprising methane from anerobic digestion process 104 is passed to methane conversion process 110, which can be any known methane conversion processes to produce $CO_2$, CO and or $H_2$ as described above. Depending upon the selected methane conversions process, stream composing oxygen 122 is also introduced to methane conversion process 110 or to mix with effluent stream 108 from anaerobic digestion process and then introduced to methane conversion process 110. Methane conversion process effluent 112 comprising $CO_2$ CO and or $H_2$ is passed to gas fermentation process 114. Gas fermentation process 114 converts a portion of the carbon in the $CO_2$ and or CO of effluent 112 into a product stream 108 comprising of at least one product that the gas fermentation process 114 is adapted to produce. To operate, the gas fermentation process 114 may require other utility inputs such as compressed air, instrument air, an electrical feed, or other utility inputs commonly known by those skilled in the art. The product stream 108 may be passed (e.g., pumped) to a metering valve 110 to determine the amount of product that is contained in product stream 108. Product stream 108 may be passed (e.g., pumped) to a storage tank (not shown) where it can be stored for short-, medium-, or long-term storage.

Multiple system comprising an anerobic digestion zone, a methane conversion zone and a gas fermentation zone can be integrated at a natural climate solution or nature-based solution site, where each system comprising an anerobic digestion zone, a methane conversion zone and a gas fermentation zone can receive the same type of biodiverse biomass carbon source. Varying different operating conditions such as pressure or temperature within the bioreactor or utilizing different microbes (e.g., aerobic or anaerobic bacteria), allows each gas fermentation process 114 to be individually adapted to output a different product in its respective product stream 108.

Gas fermentation process 114 can be configured to produce fuels, and such fuels can be utilized on-site by the natural climate solution or nature-based solution site. Such synergy allows for the site to lower the overall operating costs by decreasing the spend related to such fuels and fuel sources, thereby increasing the overall profitability of the site. Alternatively, the gas fermentation process product may be transported to a remote site for use.

Figure 2:
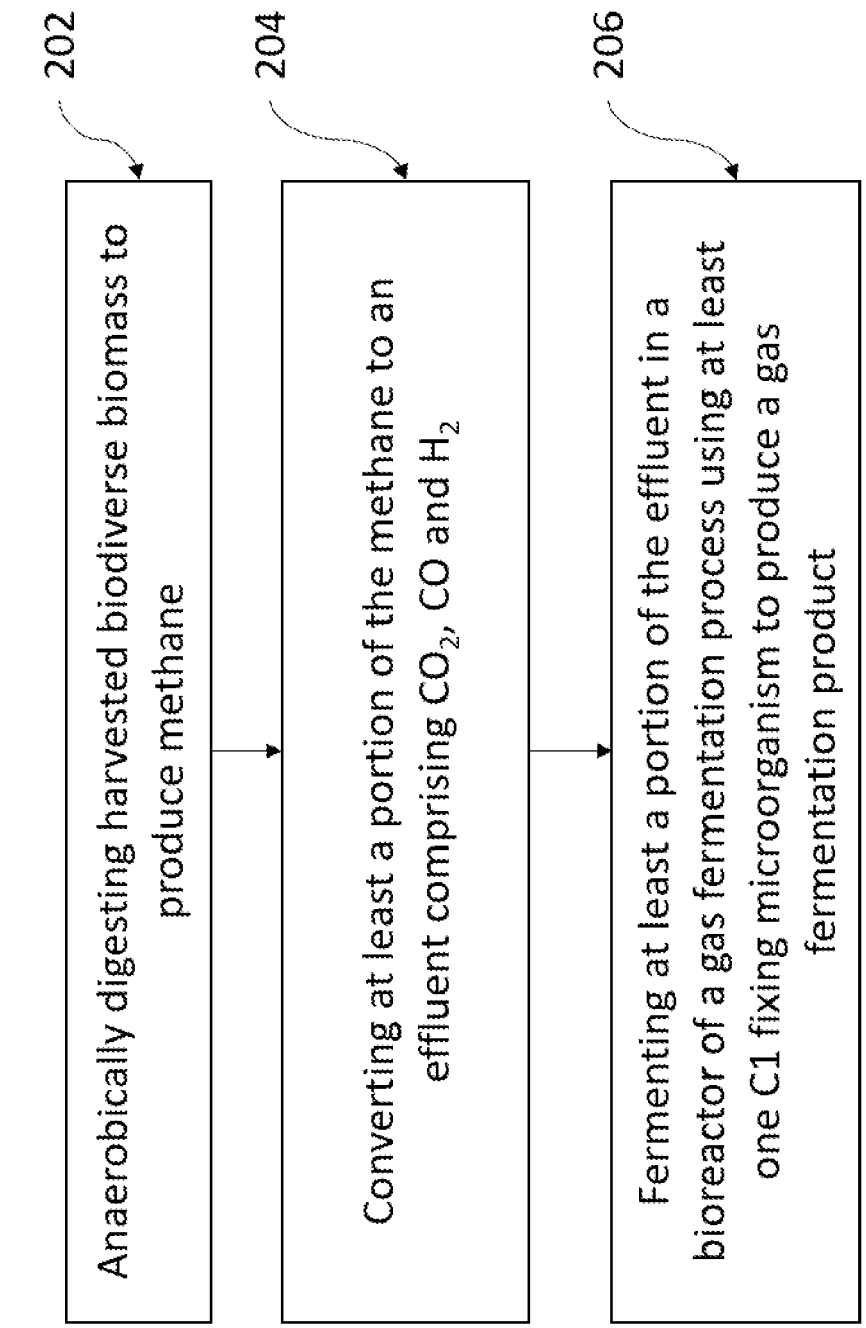
FIG. 2 is a flowchart of an embodiment of a method of using a gas fermentation process integrated within a natural climate or nature-based solution.

FIG. 2 illustrates an embodiment for a method of operation 20 includes first 202 anaerobically digested harvested biodiverse biomass to produce methane. Then converting 204 the methane to a stream comprising $CO_2$, CO, and or H2. Then fermenting 206, at least a portion of the stream comprising $CO_2$, CO and H 2 in a bioreactor of a gas fermentation process using at least one C1 fixing microorganism to product a gas fermentation product.

Figure 3:
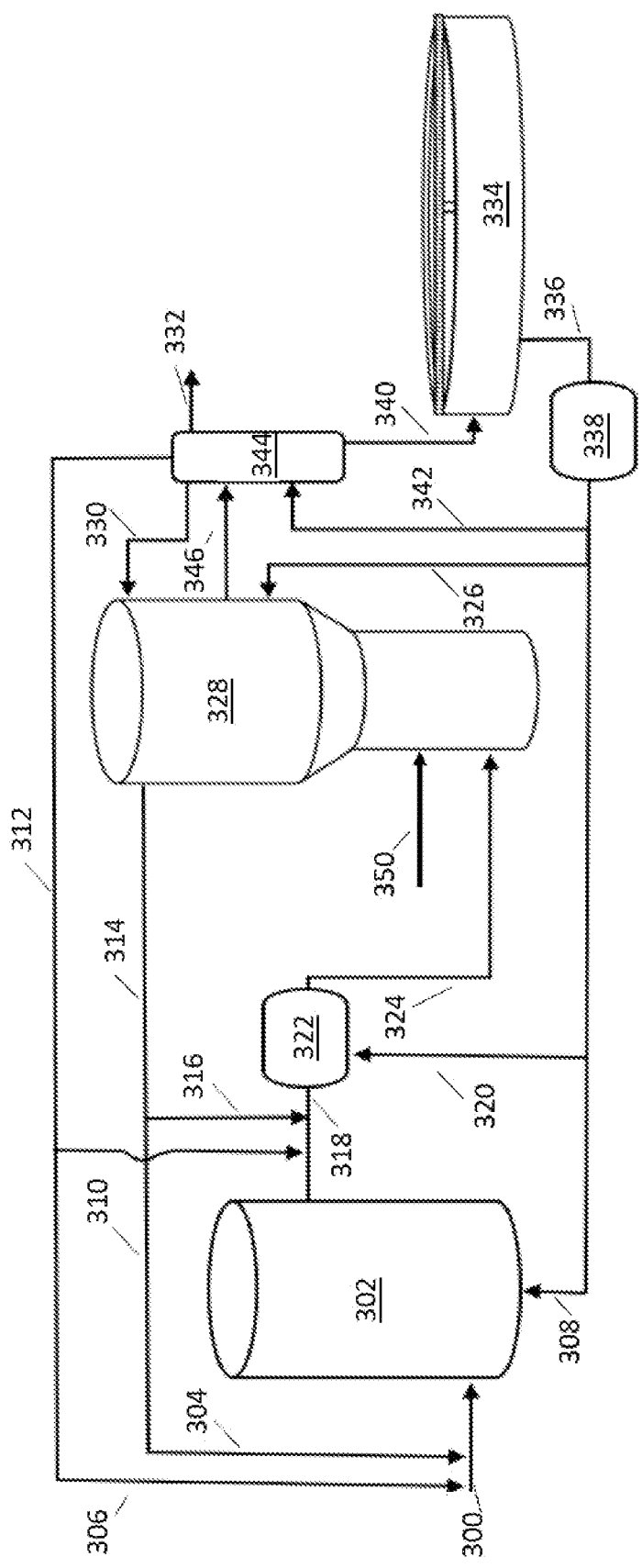
FIG. 3 is an overview of the piping and associated components of an embodiment of a gas fermentation process.

FIG. 3 shows an enlarged gas fermentation process including an optional gasification zone 302, a gas fermentation zone 328, a product recovery zone 344, and an optional wastewater treatment zone 334. Optional gasification process 302 receives a supplemental carbon source 300, which may be any suitable material capable of being gasified to produce syngas stream 302. In various instances, gasification feed 300 may be comprised at least partially of sorted and/or unsorted industrial or municipal solid waste. In other instances, the supplemental carbon source 300 is comprised at least partially of forest and/or agricultural waste. In particular embodiments, the supplemental carbon source 300 is comprised of any combination of two or more of the following: sorted municipal or industrial solid waste, unsorted municipal or industrial solid waste, forest waste, agricultural waste, or other solid or liquid waste from the refining or chemical process integrated with the enlarged gas fermentation process. In yet another embodiment, supplemental carbon source 300 is bio-derived. Integration internal to the enlarged fermentation process would also provide for at least one effluent from the fermentation process 328, at least one effluent from the product recovery process 344, and or at least one effluent from the wastewater treatment process 334 being used as gasification feed. Optional gasification zone 302 is to produce syngas as substrate for gas fermentation zone 328. If no carbon source will be gasified, gasification zone 302 is not necessary. For example, animal manure may be introduced to the anaerobic digestion process as supplemental bioderived material.

Fermentation process 30 employs at least one C1-fixing microorganism in a liquid nutrient media to ferment, in at least one fermentation bioreactor 328, the effluent 350 of the methane conversion process and optionally a gas or the syngas stream 316 and produce one or more products. The C1-fixing microorganism in fermentation bioreactor 328 may be a carboxydotrophic bacterium. In particular embodiments, the carboxydotrophic bacterium is selected from the group comprising *Moorella, Clostridium, Ruminococcus, Acetobacterium, Eubacterium, Butyribacterium, Oxobacter, Methanosarcina, Methanosarcina, Cupriavidus* and *Desulfotomaculum*. In various embodiments, the carboxydotrophic bacterium is *Clostridium autoethanogenum*.

One or more products produced in fermentation process bioreactor 328 are removed and/or separated from the fermentation broth in product recovery zone 344. Product recovery zone 344 separates and removes one or more product(s) 332 and produces at least one effluent 342, 330, 312, which comprise reduced amounts of at least one product. Product depleted effluent may be sent via a conduit 342 to wastewater treatment zone 334 to produce at least one effluent 336, which may be recycled to the gasification process 302 and/or the fermentation process 328.

In at least one embodiment, an effluent from fermentation process bioreactor 328 is tail-gas containing gas generated by the fermentation, inert gas, and or unmetabolized substrate. At least a portion of this tail gas may be passed via a conduit 314 to the gasification zone 302 to be used as part of the gasification feed 300. At least a portion of the tail gas may be sent via a conduit 316 to the gasification zone 302 to quench the syngas stream 316. At least a portion of the tail gas may be passed to the refinery or chemical manufacture process integrated with the enlarged gas fermentation process.

In at least one embodiment, the effluent from the fermentation process bioreactor 328 is fermentation broth. At least a portion of the fermentation broth may be sent via a conduit 346 to product recovery zone 344. In at least one embodiment, product recovery zone 344 separates at least a portion of the microbial biomass from the fermentation broth. In various instances, at least a portion of the microbial biomass that is separated from the fermentation broth is recycled to the fermentation process bioreactor 328 via a conduit 330. In various instances, at least a portion of the microbial biomass separated from the fermentation broth is passed via a conduit 306 to optional gasification zone 302 for use as part of gasification feed 300. In certain instances, fermentation process bioreactor 328 produces fusel oil which may also be recovered in product recovery zone 344 through any suitable means such as within the rectification column of a distillation system. In at least one embodiment, at least a portion of the fusel oil from the product recovery zone 344 is used as a heating source for one or more zones or elsewhere in the refinery or chemical process.

In various instances, at least a portion of a wastewater stream, comprising fermentation broth, which may contain microbial biomass from fermentation process bioreactor 328 may be passed via conduit 314 to optional gasification zone 302, without being passed to product recovery zone 344.

In instances where the fermentation broth is processed by the product recovery process 344, at least a portion of the microbial biomass depleted water, produced through the removal of microbial biomass from the fermentation broth, may be returned to fermentation process bioreactor 328 via a conduit 330 and/or sent via a conduit 312 to optional gasification zone 302. At least a portion of the microbial biomass depleted water may be passed via conduit 306 optional gasification zone 302 to be used as part of gasification feed 300, or ay be passed to anaerobic digestion process (not shown). At least a portion of the microbial biomass depleted water may be passed via conduit 310 to quench syngas stream 316. At least a portion of the effluent from product recovery zone 344 may be passed via a conduit 342 to wastewater treatment zone 334. The effluent from product recovery zone 344 may comprise reduced amounts of product and/or microbial biomass.

Wastewater treatment zone 334 receives and treats effluent from one or more zones to produce clarified water. The clarified water may be passed or recycled via a conduit 336 to one or more zones. For example, at least a portion of the clarified water may be passed via conduit 212 to the fermentation process bioreactor 328, at least a portion of the clarified water may be passed gasification zone 302 via conduit 232 to be used as part of the gasification feed 300 and or via conduit 222 to quench syngas stream 316. In certain instances, the wastewater treatment process 334 generates microbial biomass as part of the treatment process. At least a portion of this microbial biomass may be passed via conduit 232 to the gasification zone 302 for use as part of gasification feed 300. Wastewater treatment zone 334, as a by-product of treating microbial biomass, produces biogas. At least a portion of the biogas may be passed via conduit 336 to gasification zone 302 to be used as part of gasification feed 300 and or via a conduit 222 to quench syngas stream 316.

Optional wastewater treatment effluent removal unit 338 is positioned downstream of wastewater treatment zone 334. At least a portion of biogas from wastewater treatment zone 334 is passed to removal unit 338 to remove and/or convert at least a portion of at least one constituent found in the biogas stream. Removal unit 338 operates to lower the concentration of constituents to within preterminal allowable levels and produce a treated stream 342, 326, 320, and/or 308 suitable to be used by the subsequent one or more zones 344, 328, 322, and/or 302, respectively.

In other embodiments, multiple GF units 106 can be integrated within a natural climate solution or nature-based solution facility. The multiple GF units 106 can be adapted to produce a similar or identical product from a common or different input streams 314. The multiple GF units 106 can then have their respective outputs 108 configured to output to a single storage tank 112. This synergy can allow the production operator to capture a maximum amount of underutilized gases or streams and convert it into a marketable product. The multiple GF units 106 can operate such that all GF units utilize anaerobic bacterium, all utilize aerobic bacterium, or some utilize anaerobic while others utilize aerobic bacterium.

Figure 4:
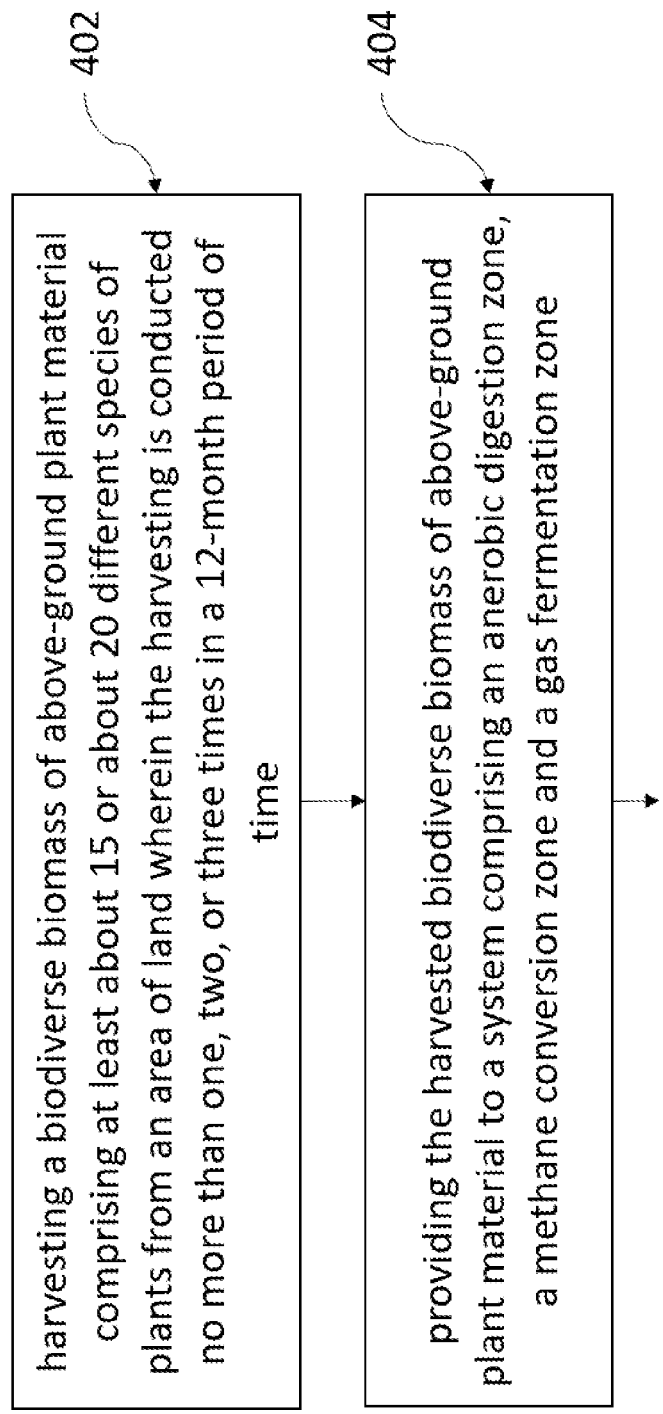
FIG. 4 is a flowchart of an embodiment of a method of providing a natural climate or nature-based solution feedstock to a system comprising an anerobic digestion zone, a methane conversion zone and a gas fermentation zone.
Figure 5:
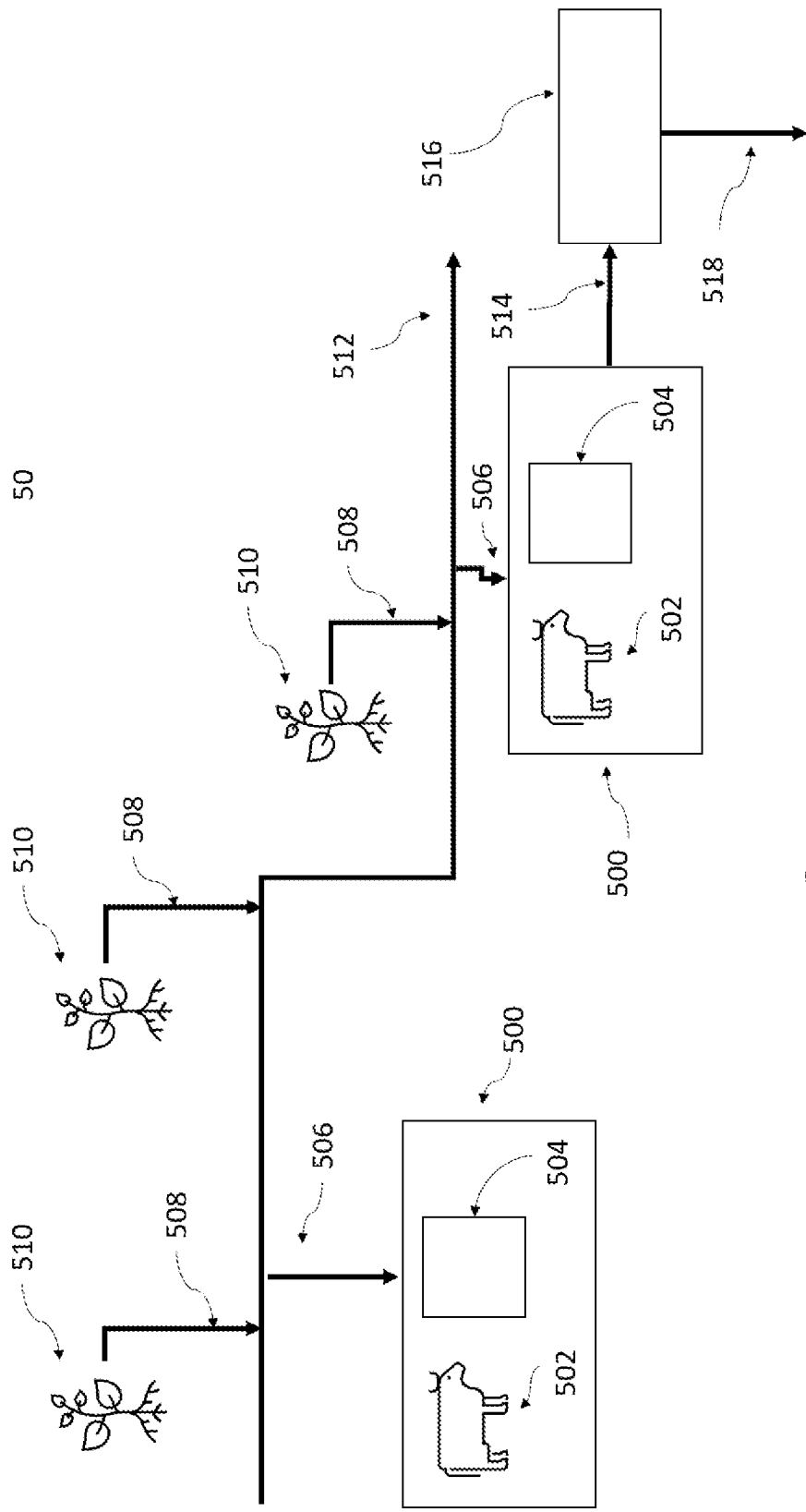
FIG. 5 is a flow scheme showing both local and distributed systems as well as optional supplemental bioderived feedstock and an optional chemical processing facility.

FIG. 4 illustrates an embodiment for a method of generating a feedstock for a system comprising an anerobic digestion zone, a methane conversion zone and a gas fermentation zone. The method includes first 402 harvesting a biodiverse biomass of above-ground plant material comprising at least about 2, 3, 5, 8, 10, 12, 15 or 20 different species of plants from an area of land wherein the harvesting is conducted no more than one, two, or three times in a 12-month period of time. Then providing 404, providing the harvested biodiverse biomass of above-ground plant material for use in a system comprising an anerobic digestion zone, a methane conversion zone and a gas fermentation zone Referring now to FIG. 5, which illustrates integrations of a system 500 comprising an anerobic digestion zone, a methane conversion zone and a gas fermentation zone and a supplemental bioderived feedstock material with a natural climate solution or nature based solution which is used to provide feedstock comprising biomass wherein the biomass comprises harvested biodiverse above-ground plant material comprising at least 2, 3, 5, 8, 10, 12, 15 or 20 different species of plants from an area of land wherein the biodiverse above-ground plant material is harvested no more than one, two, or three times in a 12 month period of time. FIG. 5 shows three locations of areas of land 510 wherein the biodiverse above-ground plant material is harvested no more than one, two, or three times in a 12-month period of time. The harvested biodiverse above-ground plant material provided as feedstock is shown as being transported 508, 506, and 512 to local or remote systems 500 comprising an anerobic digestion zone, a methane conversion zone and a gas fermentation zone 504 and a supplemental bioderived feedstock material 502 such as animal manure. At least a portion of product 514 from system 500 may be passed to a downstream processing unit 516 to generate additional downstream products 518.

Downstream processing unit 516 may be a catalytic process unit and can be a device consisting of one or more vessels and/or towers or piping arrangements, which includes continuous stirred tank reactor (CSTR), immobilized cell reactor (ICR), trickle bed reactor (TBR), bubble column, gas lift fermenter, membrane reactor such as hollow fibre membrane bioreactor (HFMBR), static mixer, or other vessel or other device suitable for gas-liquid contact, fixed bed, moving bed, simulated moving bed, fluidized bed, entrained bed, slurry reactor, packed bed, trickle bed, batch, semi batch, continuous, plug flow, flash, dense phase, fixed bed, downflow fixed bed, upflow expanded bed, and ebullating bed.

The types of catalysts used in the catalytic process unit can include, but are not limited to, natural clays, supported or unsupported metal or metal oxide containing catalysts, acid catalysts, zeolites, organometallic compounds. Examples include activated natural or synthetic material including activated, such as acid treated, natural clays such as bentonite type of synthesized silica-alumina or silica-magnesia, optionally with added oxides of zirconium, boron or thorium; mixed metal oxides supported on alumina or silica, such as tungsten-nickel sulfide or cobalt; metal and mixed metals containing catalysts such as platinum, palladium, rhenium, rhodium, copper, nickel, optionally supported on a silica or silica-alumina base; aluminum chloride, hydrogen chloride, sulfuric acid, hydrogen fluoride, phosphates, liquid phosphoric acid, phosphoric acid on kieselguhr, copper pyrophosphate pellets, phosphoric acid film on quarts, aluminosilicates, iron, vanadium, vanadium oxide on silica, nickel, silicone dioxide, carbonic anhydrase, iodine, zeolites, silver on alumina, Ziegler-natta catalysts, organometallic compounds, iron oxide stabilized by chromium oxide, copper, copper-zinc-alumina, promoted iron where the promoters can be potassium oxide, aluminum oxide, and calcium oxide, and iron-chrome.

C. Microbes and Fermentation

The disclosed systems and methods integrate microbial fermentation into nature based solution convert biodiverse biomass harvested in a mode that stimulates sequestration of carbon in the soil into useful products such as ethylene. In particular, the disclosed systems and methods are applicable for producing useful products (e.g., ethylene, ethanol, acetate, etc.) from gaseous substrates, such as gases that may optionally contain H2, that are utilized as a carbon source by microbial cultures. Such microorganisms may include bacteria, archaea, algae, or fungi (e.g., yeast), and these classes of microorganism may be suitable for the disclosed systems and methods. In general, the selection of the microorganism(s) is not particularly limited so long as the microorganism is C1-fixing, carboxydotrophic, acetogenic, methanogenic, capable of Wood-Ljundahl synthesis, a hydrogen oxidizer, autotrophic, chemolithoautotrophic, or any combination thereof. Among the various suitable classes of microorganisms, bacteria are particularly well suited for integration in the disclosed systems and methods.

When bacteria are utilized in the disclosed systems and methods, the bacteria may be aerobic or anaerobic, depending on the nature of the carbon source and other inputs being fed into the bioreactor or fermentation unit. Further, the bacteria utilized in the disclosed systems and methods can include one of more strains of carboxydotrophic bacteria. In particular embodiments, the carboxydotrophic bacterium can be selected from a genus including, but not limited to, *Cupriavidus, Clostridium, Moorella, Carboxydothermus, Ruminococcus, Acetobacterium, Eubacterium, Butyribacterium, Oxobacter, Methanosarcina, Methanosarcina,* and *Desulfotomaculum*. In particular embodiments, the carboxydotrophic bacterium is *Clostridium autoethanogenum*. In other particular embodiments, the carboxydotrophic bacterium is *Cupriavidus necator.*

A number of anaerobic bacteria are known to be capable of carrying out fermentation for the disclosed methods and system. Examples of such bacteria that are suitable for use in the invention include bacteria of the genus *Clostridium*, such as strains of *Clostridium ljungdahlii* (including those described in WO 00/68407, EP 117309, U.S. Pat. Nos. 5,173,429, 5,593,886, and 6,368,819, WO 98/00558 and WO 02/08438), *Clostridium carboxydivorans* (Liou et al., International Journal of Systematic and Evolutionary Microbiology 33: pp 2085-2091) and *Clostridium autoethanogenum* (Abrini et al., Archives of Microbiology 161: pp 345-351). Other suitable bacteria include those of the genus *Moorella*, including *Moorella* sp HUC22-1 (Sakai et al., Biotechnology Letters 29: pp 1607-1612), and those of the genus *Carboxydothermus* (Svetlichny, V. A., et al. (1991), Systematic and Applied Microbiology 14: 254-260). The disclosures of each of these publications are incorporated herein by reference. In addition, other carboxydotrophic anaerobic bacteria can be used in the disclosed systems and methods by a person of skill in the art. It will also be appreciated upon consideration of the instant disclosure that a mixed culture of two or more bacteria may be used in in the disclosed systems and methods. All of the foregoing patents, patent applications, and non-patent literature are incorporated herein by reference in their entirety.

One exemplary anaerobic bacteria that is suitable for use in the disclosed systems and methods is *Clostridium autoethanogenum*. In some embodiments, the *Clostridium autoethanogenum* is a *Clostridium autoethanogenum* having the identifying characteristics of the strain deposited at the German Resource Centre for Biological Material (DSMZ) under the identifying deposit number 19630. In some embodiments, the *Clostridium autoethanogenum* is a *Clostridium autoethanogenum* having the identifying characteristics of DSMZ deposit number DSMZ 10061. In some embodiments, the *Clostridium autoethanogenum* is a *Clostridium autoethanogenum* having the identifying characteristics of DSMZ deposit number DSMZ 23693.

In some embodiments, the anaerobic bacteria is *Clostridium carboxidivorans* having the identifying characteristics of deposit number DSM15243. In some embodiments, the anaerobic bacteria is *Clostridium drakei* having the identifying characteristics of deposit number DSM12750. In some embodiments, the anaerobic bacteria is *Clostridium ljungdahlii* having the identifying characteristics of deposit number DSM13528. Other suitable *Clostridium ljungdahlii* strains may include those described in WO 00/68407, EP 117309, U.S. Pat. Nos. 5,173,429, 5,593,886, and 6,368,819, WO 98/00558 and WO 02/08438, all of which are incorporated herein by reference. In some embodiments, the anaerobic bacteria is *Clostridium scatologenes* having the identifying characteristics of deposit number DSM757. In some embodiments, the anaerobic bacteria is *Clostridium ragsdaleii* having the identifying characteristics of deposit number ATCC BAA-622.

In some embodiments, the anaerobic bacteria is *Acetobacterium woodii*. In some embodiments, the anaerobic bacteria is from the genus *Moorella*, such as *Moorella* sp HUC22-1, (Sakai et al, Biotechnology Letters, 29: pp 1607-1612). Further examples of suitable anaerobic bacteria include, but are not limited to, Morella thermoacetica, *Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp 41-65). In addition, it should be understood that other C1-fixing, carboxydotrophic anaerobes may be suitable for the disclosed systems and methods. It will also be appreciated that a mixed culture of two or more bacteria may be utilized as well.

A number of aerobic bacteria are known to be capable of carrying out fermentation for the disclosed methods and system. Examples of such bacteria that are suitable for use in the invention include bacteria of the genus *Cupriavidus* and *Ralstonia*. In some embodiments, the aerobic bacteria is *Cupriavidus necator* or *Ralstonia eutropha*. In some embodiments, the aerobic bacteria is *Cupriavidus alkaliphilus*. In some embodiments, the aerobic bacteria is *Cupriavidus basilensis*. In some embodiments, the aerobic bacteria is *Cupriavidus campinensis*. In some embodiments, the aerobic bacteria is *Cupriavidus gilardii*. In some embodiments, the aerobic bacteria is *Cupriavidus laharis*. In some embodiments, the aerobic bacteria is *Cupriavidus metallidurans*. In some embodiments, the aerobic bacteria is *Cupriavidus nantogensis*. In some embodiments, the aerobic bacteria is *Cupriavidus numazuensis*. In some embodiments, the aerobic bacteria is *Cupriavidus oxalaticus*. In some embodiments, the aerobic bacteria is *Cupriavidus pampae*. In some embodiments, the aerobic bacteria is *Cupriavidus pauculus*. In some embodiments, the aerobic bacteria is *Cupriavidus pinatubonensis*. In some embodiments, the aerobic bacteria is *Cupriavidus plantarum*. In some embodiments, the aerobic bacteria is *Cupriavidus respiraculi*. In some embodiments, the aerobic bacteria is *Cupriavidus taiwanensis*. In some embodiments, the aerobic bacteria is *Cupriavidus yeoncheonensis*.

The fermentation may be carried out in any suitable bioreactor. In some embodiments, the bioreactor may comprise a first, growth reactor in which the microbes (e.g., bacteria) are cultured, and a second, fermentation reactor, to which fermentation broth from the growth reactor is fed and in which most of the fermentation product (e.g. ethylene, ethanol, acetate, etc.) is produced.

It will be appreciated that for growth of the bacteria and fermentation to occur, in addition to a carbon-containing substrate gas, a suitable liquid nutrient medium will need to be fed to the bioreactor. A nutrient medium will contain vitamins and minerals sufficient to permit growth of the micro-organism used. Aerobic and anaerobic media suitable for the fermentation using carbon-containing substrate gases as the sole carbon source are known in the art. For example, suitable media are described in U.S. Pat. Nos. 5,173,429 and 5,593,886 and WO 02/08438, WO2007/115157 and WO2008/115080, referred to above and all of which are incorporated herein by reference. Further, the fermentation can be carried out under appropriate conditions for the desired fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations, and maximum product concentrations to avoid product inhibition.

The optimum reaction conditions will depend partly on the particular micro-organism used. However, in general, it may be preferable that the fermentation be performed at a pressure higher than ambient pressure. Operating at increased pressures may allow for, for example, a significant increase in the rate of CO transfer from the gas phase to the liquid phase where it can be taken up by the micro-organism as a carbon source. This, in turn, means that the retention time (defined as the liquid volume in the bioreactor divided by the input gas flow rate) can be reduced when bioreactors are maintained at elevated pressure rather than atmospheric pressure. Also, since a given CO, or $CO_2$ and $H_2$ conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment.

Similarly, temperature of the culture may vary as needed. For example, in some embodiments, the fermentation is carried out at a temperature of about 34° C. to about 37° C. In some embodiments, the fermentation is carried out at a temperature of about 34° C. This temperature range may assist in supporting or increasing the efficiency of fermentation including, for example, maintaining or increasing the growth rate of bacteria, extending the period of growth of bacteria, maintaining or increasing production of the desired product (e.g., ethylene, ethanol, acetate, etc.), or maintaining or increasing CO or $CO_2$ uptake or consumption.

Culturing of the bacteria used in in the disclosed systems and methods may be conducted using any number of processes known in the art for culturing and fermenting substrates. In some embodiments a culture of a bacterium can be maintained in an aqueous culture medium. For example, the aqueous culture medium may be a minimal anaerobic microbial growth medium. Suitable media are known in the art and described for example in U.S. Pat. Nos. 5,173,429 and 5,593,886; WO 02/08438, and in Klasson et al (1992), Bioconversion of Synthesis Gas into Liquid or Gaseous Fuels, *Enz. Microb. Technol.* 14:602-608; Najafpour and Younesi (2006) Ethanol and acetate synthesis from waste gas using batch culture of *Clostridium ljungdahlii*. *Enzyme and Microbial Technology*, 38(1-2):223-228; and Lewis et al (2002), Making the connection-conversion of biomass-generated producer gas to ethanol, *Abst. Bioenergy, p.* 2091-2094.

Further general processes for using gaseous substrates for fermentation that may be utilized for the disclosed systems and methods are described in the following disclosures: WO98/00558, M. Demler and D. Weuster-Botz (2010), Reaction Engineering Analysis of Hydrogenotrophic Production of Acetic Acid by *Acetobacterium woodii*, *Biotechnology and Bioengineering*; D. R. Martin, A. Misra and H. L. Drake (1985), Dissimilation of Carbon Monoxide to Acetic Acid by Glucose-Limited Cultures of *Clostridium thermoaceticum*, *Applied and Environmental Microbiology*, 49(6):1412-1417. Further processes generally described in the following articles using gaseous substrates for fermentation may also be utilized: (i) K. T. Klasson, et al. (1991), Bioreactors for synthesis gas fermentations resources, *Conservation and Recycling*, 5:145-165; (ii) K. T. Klasson, et al. (1991), Bioreactor design for synthesis gas fermentations, *Fuel*, 70:605-614; (iii) K. T. Klasson, et al. (1992), Bioconversion of synthesis gas into liquid or gaseous fuels, *Enzyme and Microbial Technology*, 14:602-608; (iv) J. L. Vega, et al. (1989), Study of Gaseous Substrate Fermentation: Carbon Monoxide Conversion to Acetate. 2. Continuous Culture, *Biotech. Bioeng.*, 34(6):785-793; (vi) J. L. Vega, et al. (1989), Study of gaseous substrate fermentations: Carbon monoxide conversion to acetate. 1. Batch culture, *Biotech. Bioeng.*, 34(6):774-784; (vii) J. L. Vega, et al. (1990), Design of Bioreactors for Coal Synthesis Gas Fermentations, *Resources, Conservation and Recycling*, 3:149-160; all of which are incorporated herein by reference.

As noted above, while bacteria may be preferred microbes for the disclosed systems and methods, other microbes like yeast may also be suitable. For example, yeast that may be used in the disclosed systems and methods include genus *Cryptococcus*, such as strains of *Cryptococcus curvatus* (also known as *Candida curvatus*) (see Chi et al. (2011), Oleaginous yeast *Cryptococcus curvatus* culture with dark fermentation hydrogen production effluent as feedstock for microbial lipid production, *International Journal of Hydrogen Energy*, 36:9542-9550, which is incorporated herein by reference). Other suitable yeasts include those of the genera Candida, Lipomyces, Rhodosporidium, *Rhodotorula*, *Saccharomyces*, and *Yarrowia*. In addition, it should be understood that the disclosed systems and methods may utilize a mixed culture of two or more yeasts. Additional fungi that may be suitable for the disclosed systems and methods include, but are not limited to, fungi selected from Blakeslea, *Cryptococcus*, *Cunninghamella*, *Mortierella*, *Mucor*, *Phycomyces*, *Pythium*, *Thraustochytrium* and *Trichosporon*. Culturing of yeast or other fungi may be conducted using any number of processes known in the art for culturing and fermenting substrates using yeasts or fungi.

Typically, fermentation is carried out in any suitable bioreactor, such as a continuous stirred tank reactor (CTSR), a bubble column reactor (BCR) or a trickle bed reactor (TBR). Also, in some embodiments, the bioreactor may comprise a first, growth reactor in which the micro-organisms are cultured, and a second, fermentation reactor, to which fermentation broth from the growth reactor is fed and in which most of the fermentation product (e.g., ethylene, ethanol, acetate, etc.) is produced.

The disclosed systems and method may comprise a primary bioreactor and a secondary bioreactor. The efficiency of the fermentation processes may be further improved by a further process of recycling a stream exiting the secondary bioreactor to at least one primary reactor. The stream exiting the secondary bioreactor may contain unused substrates, salts, and other nutrient components. By recycling the exit stream to a primary reactor, the cost of providing a continuous nutrient media to the primary reactor can be reduced. This recycling step has the further benefit of potentially reducing the water requirements of the continuous fermentation process. The stream exiting the bioreactor can optionally be treated before being passed back to a primary reactor. For example, because yeasts generally require oxygen for growth, any media recycled from a secondary bioreactor to a primary bioreactor may need to have all oxygen substantially removed, as any oxygen present in the primary bioreactor will be harmful to an anaerobic culture in the primary bioreactor. Therefore, the broth stream exiting the secondary bioreactor may be passed through an oxygen scrubber to remove substantially all of the oxygen prior to being passed to the primary reactor. In some embodiments, biomass from a bioreactor (e.g., a primary bioreactor, secondary bioreactor, or any combination thereof) may be separated and processed to recover one or more products.

In some embodiments, both anaerobic and aerobic gases can be used to feed separate cultures (e.g., an anaerobic culture and an aerobic culture) in two or more different bioreactors that are both integrated into the same process stream.

The biodiverse biomass and or the gas used as a gas fermentation feedstock may be metered (e.g., for carbon credit calculations or mass balancing of sustainable carbon with overall products) in order to maintain control of the follow rate and amount of carbon provided to the culture. Similarly, the output of the bioreactor may be metered (e.g., for carbon credit calculations or mass balancing of sustainable carbon with overall products) or comprise a valved connection that can control the flow of the output and products (e.g., ethylene, ethanol, acetate, 1-butanol, etc.) produced via fermentation. Such a valve or metering mechanism can be useful for a variety of purposes including, but not limited to, slugging of product through a connected pipeline and measuring the amount of output from a given bioreactor such that if the product is mixed with other gases or liquids the resulting mixture can later be mass balanced to determine the percentage of the product that was produced from the bioreactor. The amount of Carbon Emission Reduction Credits or tax information based on the amount of atmospheric $CO_2$ sequestered below ground in the soil may be calculated and provided to an approved regulatory agency.

The microbes of the disclosure may be cultured with the gaseous substrate to produce one or more products. For instance, products of interest for the disclosed systems and methods can include, but are not limited to, alcohols, acids, diacids, alkanes, alkenes, alkynes, and the like. More specifically, the microbes of the present disclosure may produce or may be engineered to produce ethylene (WO 2012/026833), ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1propanol (WO 2017/066498), 1hexanol (WO 2017/066498), 1octanol (WO 2017/066498), chorismate-derived products (WO 2016/191625), 3hydroxybutyrate (WO 2017/066498), 1,3butanediol (WO 2017/066498), 2-hydroxyisobutyrate or 2-hydroxyisobutyric acid (WO 2017/066498), isobutylene (WO 2017/066498), adipic acid (WO 2017/066498), 1,3hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and monoethylene glycol (WO 2019/126400), or any combination thereof. For example, in some embodiments, the microbes may produce or may be engineered to produce one or more of the foregoing products (e.g., ethanol, acetate, 1-butanol, etc.) in addition to ethylene.

Supplemental Substrates and C1-Carbon Sources

Optional supplemental substrate and/or C1-carbon source may be a gas obtained as a by-product of an industrial process or from another source, such as combustion engine exhaust fumes, biogas, landfill gas, direct air capture, flaring, or from electrolysis. The substrate and/or C1-carbon source may be syngas generated by pyrolysis, torrefaction, or gasification. In other words, carbon in solid or liquid materials may be recycled by pyrolysis, torrefaction, or gasification to generate syngas which is used as the substrate and/or C1-carbon source in gas fermentation. The optional supplemental substrate and/or C1-carbon source may be natural gas. The optional supplemental substrate and/or C1-carbon source carbon dioxide from conventional and unconventional gas production. The optional supplemental substrate and/or C1-carbon source may be a gas comprising methane. Gas fermentation processes are flexible and any of these substrate and/or C1-carbon sources may be employed.

In certain embodiments, the industrial process source of the optional supplemental substrate and/or C1 carbon source is selected from ferrous metal products manufacturing, such as a steel manufacturing, non-ferrous products manufacturing, petroleum refining, electric power production, carbon black production, paper and pulp manufacturing, ammonia production, methanol production, coke manufacturing, petrochemical production, carbohydrate fermentation, cement making, aerobic digestion, anaerobic digestion, catalytic processes, natural gas extraction, cellulosic fermentation, oil extraction, industrial processing of geological reservoirs, processing fossil resources such as natural gas coal and oil, landfill operations, or any combination thereof. Examples of specific processing steps within an industrial process include catalyst regeneration, fluid catalyst cracking, and catalyst regeneration. Air separation and direct air capture are other suitable industrial processes. Specific examples in steel and ferroalloy manufacturing include blast furnace gas, basic oxygen furnace gas, coke oven gas, direct reduction of iron furnace top-gas, and residual gas from smelting iron. Other general examples include flue gas from fired boilers and fired heaters, such as natural gas, oil, or coal fired boilers or heaters, and gas turbine exhaust. Another example is the flaring of compounds such as at oil and gas production sites. In these embodiments, the optional supplemental substrate and/or C1-carbon source may be captured from the industrial process before it is emitted into the atmosphere, using any known method.

The optional supplemental substrate and/or C1-carbon source may be synthesis gas known as syngas, which may be obtained from reforming, partial oxidation, plasma, or gasification processes. Examples of gasification processes include gasification of coal, gasification of refinery residues, gasification of petroleum coke, gasification of biomass, gasification of lignocellulosic material, gasification of wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of landfill gas, gasification of biogas such as when biogas is added to enhance gasification of another material. Examples of reforming processes include, steam methane reforming, steam naphtha reforming, reforming of natural gas, reforming of biogas, reforming of landfill gas, reforming of coke oven gas, reforming of pyrolysis off-gas, reforming of ethylene production off-gas, naphtha reforming, and dry methane reforming. Examples of partial oxidation processes include thermal and catalytic partial oxidation processes, catalytic partial oxidation of natural gas, partial oxidation of hydrocarbons, partial oxidation of biogas, partial oxidation of landfill gas, or partial oxidation of pyrolysis off-gas.

Examples of municipal solid waste include tires, plastics, refuse derived fuel, and fibers such as in shoes, apparel, and textiles. Municipal solid waste may be simply landfill-type waste and may be sorted or unsorted. Examples of biomass may include lignocellulosic material and microbial biomass. Lignocellulosic material may include agriculture by-products, forest by-products, and some industrial by-products.

The optional supplemental feedstock may also be biomass created as by-products of "nature-based solutions" (NBS) and thus natured-based solutions may provide feedstock to the gas fermentation process. Nature-based solutions is articulated by the European Commission as solutions inspired and supported by nature, which are cost-effective, simultaneously provide environmental, social, and economic benefits and help build resilience. Such solutions bring more, and more diverse, nature and natural features and processes into cities, landscapes, and seascapes, through locally adapted, resource-efficient, and systemic interventions. Nature-based solutions must benefit biodiversity and support the delivery of a range of ecosystem services. Through the use of NBS healthy, resilient, and diverse ecosystems (whether natural, managed, or newly created) can provide solutions for the benefit of both societies and overall biodiversity. Examples of nature-based solutions include natural climate solutions or nature-based solutions (conservation, restoration and improved land management that increase carbon storage or avoid greenhouse gas emissions in landscapes and wetlands across the globe), halting biodiversity loss, socio-economic impact efforts, habitat restoration, and health and wellness efforts with respect to air and water. Biomass produced through nature-based solutions may be used as feedstock to gas fermentation processes.

As shown, the optional step of a gasification process in the overall gas fermentation process increases suitable optional supplemental feedstocks to the overall gas fermentation process as compared to gaseous feedstocks alone. Further, incentives achieved may extend beyond items such as carbon credits, and into the natural based solutions space.

The substrate and/or C1-carbon source may be a gas stream comprising methane. Such a methane containing gas may be obtained from: fossil methane emissions such as during fracking, wastewater treatment, livestock, agriculture, and municipal solid waste landfills. It is also envisioned that the methane may be burned to produce electricity or heat and the C1 by-products may be used as the substrate or carbon source. The substrate and/or C1-carbon source may be a gas stream comprising natural gas. Methane is converted to syngas in a methane conversion unit.

D. Examples

The following examples are given to illustrate the present disclosure. It should be understood that the invention is not to be limited to the specific conditions or details described in these examples.

Example 1—Conversion of Organic Acid to Corresponding Alcohol

Example 1A Conversion of Butyric Acid to Butanol in a CSTR

An eight-liter reactor was filled with 7200 ml of the media LM23 and autoclaved for 30 minutes at 121° C. While cooling down, the media was sparged with N2. The gas was switched to 95% CO, 5% CO2 prior inoculation with 160 ml of a *Clostridium autoethanogenum* culture. The bioreactor was maintained at 37° C. stirred at 200 rpm at the start of the culture. During the growth phase, the agitation was increased to 500 rpm. The pH was set to 5.5 and maintained by automatic addition of 5 M NaOH. The n-butyrate solution containing 20 g butyric acid buffered to pH 5.5 was added directly into the actively growing culture. Samples of the fermentation broth were taken at 0, 24 and 48 hours after butyric acid addition (see Table 1).

TABLE 1

Conversion of 20 g of n-Butyrate into 1-Butanol by an 8 litre culture of *C. autoethanogenum* producing acetate and ethanol in a bioreactor maintained at pH 5.5.

| Time [h] | 0 | 24 | 48 |
|---|---|---|---|
| Butanol produced [g] | 0.0 | 4.0 | 8.2 |

Starting conditions: active culture of *C. autoethanogenum*, producing acetate (8.3 g/l) and ethanol (5.4 g/l) pH 5.5 and sparging gas containing 95% CO in CO2.

Example 2—Conversion of Acetate and Butyrate to Corresponding Alcohols

Serum vials were prepared in accordance with the above. Once microbial growth was established (associated with acetate and small amounts of ethanol produced), the following compounds were added into the 50 ml active culture in the serum bottle: 1 ml of Sodium Dithionite 10 g/l solution, 2 ml of n-butyric acid solution 100 g/l (pH adjusted to 5.5 with Sodium Hydroxide 5 M). The gas phase was exchanged for 25 psig overpressure of a mixture of 95% CO, 5% CO2 gas. After addition of the acid, 1 ml sample was taken for quantification of the metabolites at various time points (see Table 2)

TABLE 2

Conversion of n-butyrate into 1-Butanol by a culture of *C. autoethanogenum* producing acetate and ethanol in a serum bottle at pH 5.5 in presence or absence of 0.8 mM methylviologen (MV).

| Time (h) | Methylviologen conc (mM) | Acetate conc (g/L) | Ethanol conc (g/L) | Butyrate conc (g/L) | Butanol conc (g/L) |
|---|---|---|---|---|---|
| 0 | 0 | 4.50 | 1.26 | 4.19 | 0.00 |
| 2 | 0 | 5.00 | 1.40 | 3.93 | 0.16 |
| 4 | 0 | 4.19 | 1.28 | 3.68 | 0.30 |
| 22 | 0 | 4.61 | 1.44 | 3.81 | 0.41 |
| 0 | 0.8 | 4.72 | 1.24 | 3.81 | 0.00 |
| 2 | 0.8 | 4.87 | 1.42 | 3.66 | 0.17 |
| 4 | 0.8 | 4.88 | 1.49 | 3.42 | 0.34 |
| 22 | 0.8 | 4.15 | 1.84 | 2.27 | 1.35 |

Starting conditions: active culture of *C. autoethanogenum*, producing acetate (4.7 g/l) and ethanol (1.2 g/l) pH 5.5, headspace: 25 psig overpressure of 95% CO in CO2.

The presence of the mediator methyl viologen significantly inhibits conversion of n-butyrate to n-butanol (Table 2).

The results illustrate a number of significant advantages over previously reported methods for the microbial conversion of acids to their corresponding alcohols. For example, it demonstrated that *Clostridium autoethanogenum* can be used to produce alcohols which it was not known to be able to produce under standard fermentation conditions.

The bacterial cells do not need to be harvested prior to addition of acid to produce a desired alcohol; the conversion of acid to alcohol is carried out directly in the culture media. This significantly reduces handling of cells, the risk of cell damage which may be caused by centrifugation and resuspension, and the risk of oxygen contamination.

The conversion does not require the use of a mediator, such as methyl viologen. In fact, the addition of methyl viologen was demonstrated to inhibit or at least reduce the rate of conversion of acids to alcohols. Such mediators are often toxic. Removing the need for a mediator has the advantage of reducing handling of toxic chemicals and reducing the costs associated with production of alcohols.

At least in the case of *C. autoethanogenum*, the bacterial cells can be maintained at the same pH and temperature during the growth phase and the acid to alcohol conversion phase (37° C. and pH 5.5). This simplifies the process and reduces the risk of shock to the cells.

Further, the addition of the acid when the bacteria are in the conversion phase, and the ability of the cells to continue to consume carbon monoxide and produce acetate and ethanol (for example) while they are converting the added acids to corresponding alcohols, provides a method in which a number of valuable products can be produced simultaneously.

Example 3—Conversion of Various Acids to Corresponding Alcohols

Serum vials were prepared in accordance with the above. However, 5 mL of an aqueous acid solution was added to the empty vial and the pH adjusted to 5.5 with NaOH. Sodium dithionate (0.5 mL of a 10 g/L aqueous solution) or cysteine (1 mL of a 6.25 g/L aqueous solution) was added prior to inoculation. Each serum vial was pressurized to 30 psig with 95% CO gas and incubated at 37° C. with constant shaking. Samples of the fermentation broth were taken at 72 h (see Table 3).

TABLE 3

Conversion of various acids to corresponding alcohols by *Clostridium autoethanogenum*.

| Reducing agent | Acid | Initial acid concentration (g/L) | Alcohol concentration at 72 h (g/L) | Alcohol |
|---|---|---|---|---|
| Sodium dithionite | Propionic | 0.9 | 0.14 | (propanol) |
| Sodium dithionite | Propionic | 1.4 | 0.38 | (propanol) |
| Sodium dithionite | Butyric | 2.3 | 0.17 | (butanol) |
| Sodium dithionite | Butyric | 3.1 | 0.52 | (butanol) |
| Sodium dithionite | Valeric | 1.0 | 0.14 | (pentanol) |
| Sodium dithionite | Valeric | 1.7 | 0.24 | (pentanol) |
| Sodium dithionite | Hexanoic | 0.9 | 0.06 | (hexanol) |
| Sodium dithionite | Hexanoic | 1.7 | 0.09 | (hexanol) |
| Cysteine | Isovaleric | 1.41 | 0.03 | (3-methylbutanol) |
| Cysteine | 2-methyl-butyric | 1.87 | 0.06 | (2-methylbutanol) |

As can be seen above, *Clostridium autoethanogenum* can be used to convert a variety of acids to their corresponding alcohols in the presence of a reducing agent. Again, this is particularly significant, as the above acids and alcohols are not known to be naturally produced metabolites of C. auto.

Example 4—Effect of CO Partial Pressure

Example 4A—Effect of the CO Partial Pressure on Alcohol Production

Serum vials were prepared in accordance with the above. Each serum vial was pressurized to 30 or 40 or 50 psia using a 95% CO in CO2 gas mixture and incubated at 37° C. with constant shaking. Samples of the fermentation broth were taken at 18 h (see Table 4)

TABLE 4

Effect of different headspace overpressures on the metabolism of a gaseous substrate comprising 95% CO in $CO_2$ by a culture of *C. autoethanogenum* in a serum bottle at pH 5.5 after 18 hours of fermentation.

| Start Overpressure | 30 psia | 40 psia | 50 psia |
|---|---|---|---|
| Acetate (g/1) | 5.4 | 5.7 | 0.2 |
| Ethanol (g/1) | 0.5 | 0.8 | 2.6 |
| Final Overpressure (psig) | 2 | 8 | 29 |
| Pressure drop (psi) | 13 | 17 | 6 |

Starting conditions: continuous culture of *C. autoethanogenum*, containing 3.3 g/l acetate and 0.0 g/l ethanol at pH 5.5.

In the bioreactor bottles at 30 psi to 40 psi, about 2 g/l acetate and 0.6 g/l ethanol were produced and the pressure drop in the headspace was about 17 psi. This indicates that a substantial amount of the CO has been used for acetate production.

Surprisingly, at 50 psi, about 3 g/l acetate was consumed and 2.6 g/l ethanol produced. The results indicate that there is an optimum threshold CO partial pressure at which acetate to alcohol conversion occurs for an extended period. As CO concentration is proportional to CO partial pressure, the results indicate there is a sufficient CO concentration threshold at which C. auto converts acids to alcohols. However, it should be noted that lower pressure systems may also convert acids to alcohol, but as CO becomes depleted acetate production prevails. Additionally, under particularly CO (or H2) depleted conditions, the culture may reconsume alcohol to produce acetate.

Example 4B—Effect of CO Partial Pressure on Alcohol Production

Based on these results, a similar fermentation was conducted using the same gaseous substrate with media supplemented with different carbon sources. Serum vials were prepared in accordance with the above. Each serum vial was pressurized to 40 or 50 psia using a 95% CO in CO2 gas mixture and incubated at 37° C. with constant shaking. A control bioreactor bottle (A) was unsupplemented, while other bottles were supplemented with some fructose (B), xylose (C) or pyruvate (D). These bottles were incubated at 37° C. with constant agitation. The metabolites and biomass concentrations, as well as the headspace overpressure and pH, were measured at the start of the fermentation and after 40 hours. Results at 40 psia are shown in Table 5 and results at 50 psia are shown in Table 6.

TABLE 5

Metabolism of 40 psia overpressure of a gaseous substrate comprising 95% CO in $CO_2$ by a culture of *C. autoethanogenum* in a serum bottle at pH 5.5 after 40 h of fermentation.

| A | Acetate | Ethanol | Biomass | Over-pressure | pH | Supplement |
|---|---|---|---|---|---|---|
| Start | 6.3 | 0.4 | 0.7 | 25 | 5.5 | — |
| End | 10.0 | 1.0 | 0.7 | 7 | 4.6 | — |
| Difference | +3.7 | +0.6 | +0.0 | −18 | −0.9 | — |

| B | Acetate | Ethanol | Biomass | Over-pressure | pH | Fructose |
|---|---|---|---|---|---|---|
| Start | 6.3 | 0.5 | 0.7 | 25 | 5.5 | 0.9 |
| End | 10.1 | 1.7 | 0.7 | 9 | 4.6 | 0.0 |
| Difference | +3.8 | +1.2 | +0.0 | −16 | −0.9 | −0.9 |

| C | Acetate | Ethanol | Biomass | Over-pressure | pH | Xylose |
|---|---|---|---|---|---|---|
| Start | 6.1 | 0.4 | 0.7 | 25 | 5.5 | 0.8 |
| End | 9.8 | 1.4 | 0.9 | 7 | 4.6 | 0.1 |
| Difference | +3.7 | +1.0 | +0.2 | −18 | −0.9 | −0.7 |

| D | Acetate | Ethanol | Biomass | Over-pressure | pH | Pyruvate |
|---|---|---|---|---|---|---|
| Start | 7.0 | 0.0 | 0.8 | 25 | 5.5 | 0.8 |
| End | 10.1 | 0.8 | 0.7 | 8 | 4.8 | 0.0 |
| Difference | +3.1 | +0.8 | −0.1 | −17 | −0.7 | −0.8 |

Starting conditions: continuous culture of *C. autoethanogenum* at dilution rate = 0.04 $h^{-1}$, continuous flow of gaseous substrate comprising 95% CO in $CO_2$ (no overpressure), producing acetate and ethanol at pH 5.5. Data for acetate, ethanol, fructose, xylose, and pyruvate are concentrations in gram per litre. Biomass is given as gram of cell dry weight per litre. Overpressure of gas in the headspace is shown in psig.

In all the bioreactor bottles at 40 psia, for all conditions tested here, about 3.5 g/l acetate and minor amounts of ethanol were produced. The pressure drop in the headspace was about 17 psig. This indicates that a substantial portion of the CO has been consumed for acetate production. The pH decreased by about 0.9 units to 4.6. In all cases, there was minimal microbial growth.

TABLE 6

Metabolism of 50 psia overpressure of a gaseous substrate comprising 95% CO in $CO_2$ by a culture of *C. autoethanogenum* in a serum bottle at pH 5.5 after 40 h of fermentation.

| A | Acetate | Ethanol | Biomass | Over-pressure | pH | Supplement |
|---|---|---|---|---|---|---|
| Start | 6.3 | 0.4 | 0.7 | 35 | 5.5 | — |
| End | 1.1 | 4.3 | 0.4 | 25 | 6.4 | — |
| Difference | −5.2 | +3.9 | −0.3 | −10 | +0.9 | — |

| B | Acetate | Ethanol | Biomass | Over-pressure | pH | Fructose |
|---|---|---|---|---|---|---|
| Start | 6.3 | 0.5 | 0.7 | 35 | 5.5 | 0.9 |
| End | 1.9 | 3.9 | 0.4 | 28 | 6.4 | 0.0 |
| Difference | −4.4 | +3.4 | −0.3 | −7 | +0.9 | −0.9 |

TABLE 6-continued

Metabolism of 50 psia overpressure of a gaseous substrate comprising 95% CO in $CO_2$ by a culture of *C. autoethanogenum* in a serum bottle at pH 5.5 after 40 h of fermentation.

| C | Acetate | Ethanol | Biomass | Over-pressure | pH | Xylose |
|---|---|---|---|---|---|---|
| Start | 6.1 | 0.4 | 0.7 | 35 | 5.5 | 0.8 |
| End | 2.8 | 3.4 | 0.4 | 30 | 6.4 | 0.0 |
| Difference | −3.3 | +3.0 | −0.3 | −5 | +0.9 | −0.8 |

| D | Acetate | Ethanol | Biomass | Over-pressure | pH | Pyruvate |
|---|---|---|---|---|---|---|
| Start | 7.0 | 0.0 | 0.8 | 35 | 5.5 | 0.8 |
| End | 1.5 | 4.5 | 0.4 | 26 | 6.5 | 0.0 |
| Difference | −5.5 | +4.5 | −0.4 | −9 | +1.0 | −0.8 |

Starting conditions: continuous culture of *C. autoethanogenum* at dilution rate = 0.04 $h^{-1}$, continuous flow of gaseous substrate comprising 95% CO in $CO_2$ (no overpressure), producing acetate and ethanol at pH 5.5. Data for acetate, ethanol, fructose, xylose, and pyruvate are concentrations in gram per litre. Biomass is given as gram of cell dry weight per litre. Overpressure of gas in the headspace is shown in psig.

In all the bioreactor bottles at 50 psia, for all conditions tested here, significant amounts of acetate were consumed, and more than 3 g/l ethanol was produced. There is a strong correlation between acetate consumption and ethanol production. Acetate consumption/ethanol production occurs in such a way that for each mole of acetate consumed approximately one mole of ethanol was produced (Table 7). However, the supplemented carbohydrate (or pyruvate) was substantially consumed, and the biomass levels, estimated by optical density, decreased. In each instance, the pressure drop in the headspace was below 10 psi. In all cases, the pH increased by about 0.9 units to 6.4.

TABLE 7

Molar ratios for batch fermentation at 35 psi overpressure, based on results shown in Table 2 and 3.

| | Gas only | Gas and fructose | Gas and xylose | Gas and pyruvate |
|---|---|---|---|---|
| 1. Acetate consumed/ Acetate at start | 0.83 | 0.70 | 0.54 | 0.79 |
| 2. Ethanol produced/ Acetate at start | 0.81 | 0.70 | 0.64 | 0.84 |
| 3. Ethanol produced/ Acetate consumed | 0.98 | 1.01 | 1.19 | 1.07 |

Given the acetate consumed/acetate at start (row 1), at least 50% and in some cases over 75% of the acetate present in the fermentation broth is consumed at elevated pressure. Given the ethanol produced/acetate at start (row 2), at least 60% and in some cases at least 80% of the consumed acid is replaced by alcohol. Given ethanol produced/acetate consumed (row 3), there is a strong correlation between the amount of acetate consumed in the fermentation process, and the alcohol produced. The theoretical level of dissolved CO in the media at 40 and 50 psia headspace overpressure was calculated in Table 8 based on the Henry's law.

TABLE 8

Calculation of the dissolved CO concentration in media at different headspace overpressure of a gaseous substrate comprising 95% CO in $CO_2$.

| | | | |
|---|---|---|---|
| Overpressure in headspace | psia | 40 | 50 |
| Partial pressure of CO in headspace | psi | 37.7 | 47.2 |
| Dissolved CO concentration in media | mmol/l | 2.43 | 3.05 |

Henry's constant for CO in water at 298K is 1052.6 L · atm · $mol^{-1}$

The results presented here demonstrate that there is a CO partial pressure above which the metabolism of C. autoethanogenum changes substantially from production of acetate and biomass from the CO substrate to the conversion of at least a portion of acetate into ethanol. Thus, for a CO partial pressure below 37 psi, acetate and biomass are the major products of CO gas metabolism and pH becomes acidic, and further growth is inhibited. When the CO partial pressure is above 37 psi, biomass growth and acetate production appears to be inhibited, and consumption of acetate occurs. Furthermore, ethanol production occurs with minor CO consumption. At the same time, pH increases until it reaches 6.5, where the bacteria appear to be substantially inhibited and the conversion of acetate to ethanol stops. There is no noticeable effect of fructose, xylose or pyruvate at the concentration tested.

Example 4C—Effect of CO Partial Pressure on Alcohol Production

Serum vials were prepared in accordance with the above. Each serum vial was pressurized to 25 psig (40 psia) with the indicated gas and incubated at 37° C. with constant shaking. Samples of the fermentation broth were taken at intervals of 1 h, 3 h and 5 h (see Table 9).

TABLE 9

Conversion of acetate to alcohol at various CO partial pressures by Clostridium autoethanogenum over 5 hours.

| Gas composition | Time | Acetate conc (g/L) | Ethanol conc (g/L) | Pressure (psig) |
|---|---|---|---|---|
| 100% CO | 0 | 11.914 | 0 | 25 |
| | 1 | 11.273 | 0.523 | 25.1 |
| | 3 | 10.488 | 1.295 | 22.7 |
| | 5 | 10.337 | 1.518 | 21.4 |
| 90% CO; 10% N2 | 0 | 11.914 | 0 | 25 |
| | 1 | 11.177 | 0.548 | 23.3 |
| | 3 | 10.407 | 1.315 | 21.2 |
| | 5 | 10.12 | 1.602 | 19.5 |
| 80% CO; 20% N2 | 0 | 11.914 | 0 | 25 |
| | 1 | 11.389 | 0.44 | 23.9 |
| | 3 | 11.042 | 1.055 | 22.5 |
| | 5 | 10.605 | 1.267 | 21.3 |
| 70% CO; 30% N2 | 0 | 11.914 | 0 | 25 |
| | 1 | 11.341 | 0.538 | 25.8 |
| | 3 | 10.51 | 1.193 | 23.4 |
| | 5 | 10.579 | 1.445 | 21.8 |
| 60% CO; 40% N2 | 0 | 11.914 | 0 | 25 |
| | 1 | 11.311 | 0.565 | 26.3 |
| | 3 | 10.959 | 1.297 | 23.5 |
| | 5 | 10.493 | 1.5 | 21.6 |
| 50% CO; 50% N2 | 0 | 11.9 | 0 | 25 |
| | 1 | 11.3 | 0.533 | 25.9 |
| | 3 | 11.0 | 1.236 | 23.5 |
| | 5 | 10.5 | 1.448 | 21.9 |

The results indicate that the sufficient threshold CO partial pressure at which acids are converted to alcohols is less than 20 psia. Over a short reaction time scale (c.f. Examples 4A-C), acetate is converted to alcohol substantially stoichiometrically at all CO partial pressures tested. Accordingly, a CO partial pressure over 20 psia is sufficient for C. auto to convert acids to alcohols.

Example 5—Effect of Gas Composition

Example 5A—Effect of Pure Gas on Acetate Conversion to Ethanol

Serum vials were prepared in accordance with the above. Each serum vial was pressurized to 25 psig (40 psia) with the indicated gas and incubated at 37° C. with constant shaking. Samples of the fermentation broth were taken at intervals of 1 h, 3 h and 5 h (see Table 10).

TABLE 10

Conversion of acetate to ethanol by Clostridium autoethanogenum using alternative gas compositions.

| Gas composition | Time | Acetate conc (g/L) | Ethanol conc (g/L) | Pressure (psig) |
|---|---|---|---|---|
| 100% N2 | 0 | 12.531 | 0.133 | 26.1 |
| | 1 | 12.742 | 0 | 27.5 |
| | 3 | 12.394 | 0 | 27.1 |
| | 5 | 12.551 | 0 | 26.6 |
| 100% H2 | 0 | 12.531 | 0.133 | 25.8 |
| | 1 | 11.921 | 0.384 | 24.8 |
| | 3 | 11.811 | 0.527 | 23.3 |
| | 5 | 11.998 | 0.546 | 22.5 |
| Steel Mill Waste Gas (approx. 53% CO; 18% CO2; 26% N2; 3% H2) | 0 | 12.531 | 0.133 | 24.8 |
| | 1 | 11.256 | 1.007 | 23.6 |
| | 3 | 10.668 | 1.605 | 20.6 |
| | 5 | 11.688 | 1.362 | 16.7 |

The results clearly indicate a reducing gas, such as CO or H2 is necessary in order for C. auto to convert acids to alcohols. It is considered that hydrogen can be used in place of CO as the metabolic pathway from acids to alcohols includes hydrogenase enzymes. It is further considered that while H2 is a suitable energy source for converting acids to alcohols it would not be adequate for biosynthesis and/or acetate production, which requires a carbon source as well as an energy source.

Example 5B—Effect of Gas Composition on Ethanol Production

Serum vials were prepared in accordance with the above. However, prior to inoculation, the vials were spiked with butyric acid solution buffered to pH 5.5 with NaOH(aq). Initial concentrations at t=0 were acetate 6.7 g/l and butyrate 0.8 g/L (no ethanol or butanol was present). Samples of the fermentation broth were taken at 24 h (see Table 11).

TABLE 11

Conversion of acids to alcohols under different CO partial pressures by Clostridium autoethanogenum, in the presence and absence of hydrogen.

| Gas composition | Acetate conc (g/L) | Ethanol conc (g/L) | Butyrate conc (g/L) | Butanol conc (g/L) |
|---|---|---|---|---|
| 100% CO (40 psia) | 4.7 | 1.8 | 0.4 | 0.3 |
| 100% CO (50 psia) | 4.2 | 1.9 | 0.3 | 0.4 |
| 75% CO 25% H2 (40 psia) | 5.5 | 1.3 | 0.5 | 0.2 |
| 60% CO 40% H2 (50 psia) | 5.0 | 1.6 | 0.5 | 0.5 |

Acids, such as butyric and acetic acids, can be converted to alcohols including ethanol and butanol in the presence of mixed CO/H2 substrates. Clearly, in the absence of H2, increased CO partial pressure improves overall conversion. However, the presence of H2, particular at elevated partial pressure also improves overall conversion.

Example 5C—Effect of Gas Composition on Ethanol Production

Serum vials were prepared in accordance with the above. Each serum vial was pressurized to 35 psig (50 psia) with the indicated gas and incubated at 37° C. with constant shaking. Samples of the fermentation broth were taken at 18 h see Table 12).

TABLE 12

Conversion of acetate into ethanol under different CO partial pressures by Clostridium autoethanogenum, in the presence and absence of hydrogen.

| Gas composition | Change in acetate conc (g/L) | Change in alcohol conc (g/L) | End gas pressure (psia) CO | H2 | CO2 |
|---|---|---|---|---|---|
| 100% CO | −1.6 | +2.3 | 37 | — | 9 |
| 40% CO; 40% H2; 20% N2 | −1.2 | +2.5 | 0 | 8 | 11 |

Mixed substrates comprising CO and H2 can be used to convert acids to alcohols in the presence of C. autoethanogenum. Interestingly, over the time scale of the experiment, significantly more alcohol is produced than acetate is consumed. This indicates that while acetate may be stoichiometrically converted into ethanol, additional acetate accumulates and may be converted to alcohol until CO is completely consumed.

Example 5D—Effect of CO and H2 Partial Pressure on Alcohol Production

Serum vials were prepared in accordance with the above. Each serum vial was pressurized to 35 psig (50 psia) with the indicated gas and incubated at 37° C. with constant shaking. Samples of the fermentation broth were taken at intervals of 1.5 h, 3 h, 5 h and 24 h (see Table 13).

TABLE 13

Conversion of acetate into ethanol under different CO and H2 partial pressures by Clostridium autoethanogenum

| Gas composition | Time | Acetate conc (g/L) | Ethanol conc (g/L) | Pressure (psig) |
|---|---|---|---|---|
| 80% CO; 20% H2 | 0 | 10.8 | 0.2 | 35 |
| | 1.5 | 9.5 | 1.6 | 34.8 |
| | 3.25 | 9.3 | 2.4 | 32.2 |
| | 4.75 | 9.2 | 2.6 | 30.3 |
| | 6.75 | 9.4 | 2.5 | 28.7 |
| | 23 | 13.7 | 0.8 | 21.6 |
| 60% CO; 40% H2 | 0 | 10.8 | 0.2 | 35 |
| | 1.5 | 9.5 | 1.7 | 34.1 |
| | 3.25 | 9.5 | 2.6 | 30.6 |
| | 4.75 | 9.4 | 3.0 | 28.2 |
| | 6.75 | 9.5 | 3.1 | 25.4 |
| | 23 | 10.2 | 3.9 | 12.6 |

The results indicate that at elevated H2 levels, there is an improvement in overall conversion of acids into alcohols. However, it is considered that ethanol is reconverted back to acetate as H2 levels deplete over the course of the experiment, particularly at low levels of H2 (e.g. 20%).

Example 5E—Effect of CO Partial Pressure in Steel Mill Waste Gas

Serum vials were prepared in accordance with the above. Each serum vial was pressurized to 25 psig (40 psia) with steel mill waste gas (approx. 53% CO; 18% CO2; 26% N2; 3% H2) and incubated at 37° C. with constant shaking. Samples of the fermentation broth were taken at intervals of 1 h, 3 h and 5 h (see Table 14).

TABLE 14

Conversion of acetate to ethanol at different CO partial pressures using steel mill waste gas.

| Initial Gas Pressure | Time | Acetate conc (g/L) | Ethanol conc (g/L) | Pressure (psig) | |
|---|---|---|---|---|---|
| 46 psia | 0 | 14.217 | 0.224 | 31 | 13.053 |
| | 1 | 13.335 | 0.696 | 31.2 | |
| | 3 | 12.775 | 1.811 | 26.4 | |
| | 5 | 13.053 | 2.197 | 21.2 | |
| 40 psia | 0 | 14.217 | 0.224 | 25 | |
| | 1 | 13.395 | 0.665 | 26.1 | |
| | 3 | 12.896 | 1.77 | 21.2 | |
| | 5 | 14.012 | 1.675 | 15.6 | |
| 30 psia | 0 | 14.217 | 0.224 | 15 | |
| | 1 | 13.485 | 0.623 | 15.9 | |
| | 3 | 12.909 | 1.742 | 11.9 | |
| | 5 | 14.363 | 1.364 | 8.2 | |

Steel mill waste gases can be used to convert acids into alcohols. Increasing CO partial pressure in the waste gas, has a beneficial effect on acid conversion.

Example 5F—Effect of CO2 Partial Pressure on Ethanol Production

Serum vials were prepared in accordance with the above. Each serum vial was pressurized to 35 psig (50 psia) with the indicated gas and incubated at 37° C. with constant shaking. Samples of the fermentation broth were taken at intervals of 1 h, 3 h and 5 h (see Table 15).

TABLE 15

Conversion of acetate to ethanol at different CO2 partial pressures by *Clostridium autoethanogenum*.

| Gas composition | Time | Acetate conc (g/L) | Ethanol conc (g/L) | Pressure (psig) |
|---|---|---|---|---|
| 40% CO; 60% N2 | 0 | 9.256 | 0 | 35 |
| | 1 | 8.798 | 0.502 | 35.3 |
| | 3 | 8.31 | 1.076 | 33.3 |
| | 5 | 7.89 | 1.478 | 30.9 |
| 40% CO; 50% N2; 10% CO2 | 0 | 9.256 | 0 | 35 |
| | 1 | 8.721 | 0.509 | 35 |
| | 3 | 8.078 | 1.092 | 33.4 |
| | 5 | 7.69 | 1.511 | 31.1 |
| 40% CO; 40% N2; 20% CO2 | 0 | 9.256 | 0 | 35 |
| | 1 | 8.778 | 0.488 | 35.4 |
| | 3 | 8.115 | 1.057 | 32.9 |
| | 5 | 7.383 | 1.461 | 31.2 |
| 40% CO; 30% N2; 30% CO2 | 0 | 9.256 | 0 | 35 |
| | 1 | 8.763 | 0.473 | 34 |
| | 3 | 8.12 | 0.994 | 32.8 |
| | 5 | 7.769 | 1.4 | 31 |
| 40% CO; 20% N2; 40% CO2 | 0 | 9.256 | 0 | 35 |
| | 1 | 8.761 | 0.465 | 34 |
| | 3 | 8.191 | 0.962 | 32.9 |
| | 5 | 7.771 | 1.366 | 30.6 |
| 40% CO; 10% N2; 50% CO2 | 0 | 9.256 | 0 | 35 |
| | 1 | 9.255 | 0 | 34.5 |
| | 3 | 9.527 | 0.106 | 34 |
| | 5 | 9.131 | 0.235 | 33 |
| 40% CO; 60% CO2 | 0 | 9.256 | 0 | 35 |
| | 1 | 8.814 | 0.384 | 32.2 |
| | 3 | 8.23 | 0.737 | 31.5 |
| | 5 | 8.365 | 1.046 | 30 |

Substrates comprising CO containing a variety of constituents can be used to convert acids into alcohols. However, it is noted that increased levels of CO2 have a slight inhibitory effect on alcohol production.

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology.

All patents, patent applications, and published references cited herein are hereby incorporated by reference in their entirety. The claims are intended to cover the components and steps in any sequence which is effective to meet the objectives there intended unless the context specifically indicates the contrary. Unless the context requires otherwise, throughout this description and the claims, the words "comprise", "comprising", and the like, are to be construed in an inclusive sense as opposed to an exclusive or exhaustive sense, that is to say, in the sense of including, but not limited to.

The use of the terms "a" and "an" and "the" and similar terms are to be construed to cover both the singular and the plural, unless otherwise indicated herein or clearly contradicted by context. The terms "comprising," "having," "including," and "containing" are to be construed as open-ended terms unless otherwise noted. The use of the alternative, such as the term "or", should be understood to mean either one, both, or any combination thereof of the alternatives. Percentages are in wt. % unless otherwise stated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the invention, and does not pose a limitation on the scope of the invention unless otherwise claimed. No language in the specification should be construed as indicating any non-claimed element as essential to the practice of the invention.

Various embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EMBODIMENTS OF THE DISCLOSURE

Embodiment 1. A method comprising:
a. introducing a feedstock to an anerobic digestion zone to generate at least a biogas effluent comprising methane, wherein the feedstock comprises biomass and optionally supplemental bio-derived material, and wherein the biomass comprises harvested biodiverse above-ground plant material comprising at least about 2, 3, 5, 8, 10, 12, 15 or 20 different species of plants from an area of land wherein the biodiverse above-ground plant material is harvested no more than one, two, or three times in a 12 month period of time;
b. passing a stream comprising oxygen and at least a portion of the biogas effluent to a methane conversion zone operating at methane conversion conditions to generate a syngas stream comprising $CO_2$, CO, and $H_2$;
c. passing the syngas stream to a microbial gas fermentation zone comprising at least one C1 fixing microorganism and a nutrient solution in at least one bioreactor;
d. culturing the C1 fixing microorganism in the bioreactor by fermentation to generate a fermentation broth comprising at least one chemical product; and
e. separating the at least one chemical product from the fermentation broth.

Embodiment 2. The method of embodiment 1 wherein the area of land is grasslands.

Embodiment 3. The method of embodiment 1 wherein the area of land is prairie.

Embodiment 4. The method of any of embodiments 1 to 3 wherein the supplemental bio-derived material is animal waste, agricultural waste, forestry waste, sewage, food waste, brewery grain byproducts, organic industry waste, seaweed, plankton, algae, fish, fish waste, potato waste, sugar cane waste, sugar beet waste, straw, paper waste, manure, sawdust, wood, leaves, vegetables, nut shells, cotton trash, rice hulls, orange peels, poultry lotter, dairy manure, paper sludge, sewage sludge, sawdust, wood, leaves, vegetables, nut shells, straw, cotton trash, rice hulls, orange peels, poultry litter, dairy manure, other manures, paper sludge, distillers grain, and sewage sludge, residential compost, industrial compost or any combinations thereof.

Embodiment 5. The method of any of embodiments 1 to 4 wherein the ratio of biodiverse biomass and supplemental bioderived material varies according to when the biodiverse biomass is harvested.

Embodiment 6. The method of any of embodiments 1 to 5 wherein the anerobic digestion zone, the methane conversion zone and the gas fermentation zone are co-located with the area of land or a source of the supplemental bioderived material, or both.

Embodiment 7. The method of any one of embodiments 1 to 6 wherein the anerobic digestion zone, the methane conversion zone, and the gas fermentation zone and the area of land are within 1 mile, within 2 miles, within 3 miles, within 4 miles, or within 5 miles of each other.

Embodiment 8. The method of any of embodiments 1 to 7 wherein the feedstock does not undergo a drying procedure before introducing to an anerobic digestion zone.

Embodiment 9. The method of any of embodiments 1 to 8 wherein the anerobic digestion zone, the methane conversion zone and the gas fermentation zone are co-located with the area of land wherein the biodiverse above ground plant material is harvested.

Embodiment 10. The method of any of embodiments 1 to 9 wherein the anerobic digestion zone, the methane conversion zone and the gas fermentation zone are located remote from the area of land wherein the biodiverse above ground plant material is harvested.

Embodiment 11. The method of any of embodiments 1 to 10, wherein the C1-fixing microorganism is aerobic or anaerobic.

Embodiment 12. The method of any of embodiments 1 to 11, wherein the C1-fixing microorganism is selected from a genus of *Clostridium, Moorella, Carboxydothermus, Ruminococcus, Acetobacterium, Eubacterium, Butyribacterium, Oxobacter, Methanosarcina, Methanosarcina, Desulfotomaculum,* and *Cupriavidus*.

Embodiment 13. The method of any of embodiments 1 to 12, further comprising the step of determining the mass of the gas fermentation product, the mass of the feedstock, or both.

Embodiment 14. The method of any of embodiments 1 to 13, wherein the at least one product is selected from an alcohol, an acid, a diacid, an alkene, a terpene, an isoprene, and alkyne.

Embodiment 15. The method of any of embodiments 1 to 14, wherein the gas fermentation product is selected from ethylene, ethanol, propane, acetate, 1-butanol, butyrate, 2,3-butanediol, lactate, butene, butadiene, methyl ethyl ketone (2-butanone), acetone, isopropanol, a lipid, 3-hydroxypropionate (3-HP), a terpene, isoprene, a fatty acid, 2-butanol, 1,2-propanediol, 1propanol, 1hexanol, 1octanol, chorismate-derived products, 3hydroxybutyrate, 1,3butanediol, 2-hydroxyisobutyrate or 2-hydroxyisobutyric acid, isobutylene, adipic acid, 1,3hexanediol, 3-methyl-2-butanol, 2-buten-1-ol, isovalerate, isoamyl alcohol, and monoethylene glycol, or any combination thereof.

Embodiment 16. The method of any of embodiments 1 to 15 further comprising generating a first wastewater stream from the anaerobic digestion zone and a second wastewater stream from the gas fermentation zone and treating both the first and second wastewater streams in a wastewater treatment system.

Embodiment 17. The method of any of embodiments 1 to 16 wherein the harvested biodiverse above-ground plant material resulted in the stimulation of the sequestration of atmospheric $CO_2$ below ground in the soil.

Embodiment 18. The method of any of embodiments 1 to 17 wherein the harvested biodiverse above-ground plant material resulted in the stimulation of the sequestration of atmospheric $CO_2$ below ground in the soil and the generation of Carbon Emission Reduction Credits.

Embodiment 19. The method of any of embodiments 1 to 18 wherein the harvested biodiverse above-ground plant material resulted in the stimulation of the sequestration of atmospheric $CO_2$ below ground in the soil and the generation of measured Carbon Emission Reduction Credits.

Embodiment 20. The method of any of embodiments 1 to 19 further comprising generating solids in the anerobic digestion zone for use as soil amendments.

Embodiment 21. The method of any of embodiments 1 to 20 further comprising providing the at least one chemical product to a chemical processing facility.

Embodiment 22. The method of any of embodiments 1 to 21 further comprising passing the at least one chemical product to a chemical processing facility selected from an olefins plant, a poly-olefins plant, a polypropylene plant, a polyethylene plant, a polymer plant, a high-density polyethylene plant, an oligomers plant, a nitriles plant, an oxides plant, a topping refinery, a hydro-skimming refinery, a conversion refinery, a deep conversion refinery, a coking unit, a stream cracker, or a styrenics plant.

Embodiment 23. The method of any of embodiments 1 to 22 wherein the chemical processing facility is co-located with the anerobic digestion zone, the methane conversion zone, and the gas fermentation zone.

Embodiment 24. The method of any of embodiments 1 to 23 wherein the anerobic digestion zone, the methane conversion zone, and the gas fermentation zone and the chemical processing facility are within 1 mile, within 2 miles, within 3 miles, within 4 miles, or within 5 miles of each other.

Embodiment 25. The method of any of embodiments 1 to 24 further comprising storing the at least one product.

Embodiment 26. A method of generating a feedstock for a system comprising an anerobic digestion zone, a methane conversion zone and a gas fermentation zone, the method comprising:
  a. harvesting a biodiverse biomass of above-ground plant material comprising at least about 2, 3, 5, 8, 10, 12, 15 or 20 different species of plants from an area of land wherein the harvesting is conducted no more than one, two, or three times in a 12-month period of time; and
  b. providing the harvested biodiverse biomass of above-ground plant material for use in a system comprising an anerobic digestion zone, a methane conversion zone and a gas fermentation zone.

Embodiment 27. The method of embodiment 26 wherein the area of land is grasslands.

Embodiment 28. The method of embodiment 26 wherein the area of land is prairie.

Embodiment 29. The method of any of embodiments 26 to 28 wherein the harvesting stimulates the sequestration of atmospheric $CO_2$ below ground in the soil.

Embodiment 30. The method of any of embodiments 26 to 29 wherein the sequestration of atmospheric $CO_2$ below ground in the soil results in the generation of Carbon Emission Reduction Credits.

Embodiment 31. The method of any of embodiments 26 to 30 further comprising measuring the amount of $CO_2$ sequestered below ground in the soil.

Embodiment 32. The method of any of embodiments 26 to 31 further comprising calculating Carbon Emission Reduction Credits based on the amount of atmospheric $CO_2$ sequestered below ground in the soil and providing the calculated Carbon Emission Reduction Credits to an approved regulatory agency.

Embodiment 33. The method of any of embodiments 26 to 32 wherein the anerobic digestion zone, the methane conversion zone and the gas fermentation zone are co-located with the area of land wherein the biodiverse above ground plant material is harvested.

Embodiment 34. The method of any of embodiments 26 to 33 wherein the anerobic digestion zone, the methane conversion zone and the gas fermentation zone are located remote from the area of land wherein the biodiverse above ground plant material is harvested.

Embodiment 35. The method of any one of embodiments 26 to 34, further comprising the step of determining the mass of the harvested diverse biomass.

Embodiment 36. The method of any one of embodiments 26 to 35, further comprising the step of determining the Carbon Emission Reduction Credit resulting from the sequestration of carbon in the soil.

Embodiment 37. The method of any of embodiments 26 to 36 wherein the anerobic digestion zone, the methane conversion zone, and the gas fermentation zone are co-located with the area of land.

Embodiment 38. The method of any of embodiments 26 to 37 wherein the anerobic digestion zone, the methane conversion zone, and the gas fermentation zone and the area of land are within 1 mile, within 2 miles, within 3 miles, within 4 miles, or within 5 miles of each other.

The invention claimed is:

1. A method comprising:
   a) introducing a feedstock to an anerobic digestion process to generate at least a biogas effluent comprising methane, wherein the feedstock comprises biomass and optionally supplemental bio-derived material, wherein the biomass comprises harvested biodiverse above-ground plant material comprising at least about 10, 12, 15 or 20 different species of plants from a prairie or grassland; wherein the biodiverse above-ground plant material is harvested no more than one, two, or three times in a 12 month period of time; and wherein harvesting the biodiverse above-ground plant material no more than one, two, or three times in a 12 month period of time stimulates sequestration of atmospheric CO2 in soil of the prairie or grassland;
   b) passing a stream comprising oxygen and at least a portion of the biogas effluent to a methane conversion process operating at methane conversion conditions to generate a syngas stream comprising $CO_2$, CO, and $H_2$;
   c) passing the syngas stream to a microbial gas fermentation process comprising at least one C1 fixing microorganism and a nutrient solution in at least one bioreactor;
   d) culturing the C1 fixing microorganism in the bioreactor by fermentation to generate a fermentation broth comprising at least one chemical product; and
   e) separating the at least one chemical product from the fermentation broth;
   wherein the anerobic digestion process, the methane conversion process, and the microbial gas fermentation process are co-located with the prairie or grassland.

2. The method of claim 1 wherein the supplemental bio-derived material is animal waste, agricultural waste, forestry waste, sewage, food waste, organic industry waste, residential compost, industrial compost or any combination thereof.

3. The method of claim 1 wherein the ratio of biodiverse biomass and supplemental bioderived material varies according to when the biodiverse biomass is harvested.

4. The method of claim 1 wherein the anerobic digestion process, the methane conversion process and the gas fermentation process are co-located with a source of the supplemental bioderived material.

5. The method of claim 1 wherein the feedstock does not undergo a drying procedure before the introducing to an anerobic digestion process.

6. The method of claim 1, wherein the C1-fixing microorganism is aerobic or anaerobic.

7. The method of claim 1, wherein the at least one product is selected from an alcohol, an acid, a diacid, an alkene, a terpene, an isoprene, and an alkyne.

8. The method of claim 1 wherein the harvested biodiverse above-ground plant material generates Carbon Emission Reduction Credits.

9. The method of claim 1 wherein the supplemental bio-derived material is brewery grain byproducts, seaweed, plankton, algae, fish waste, potato waste, sugar cane waste, sugar beet waste, straw, paper waste, manure, sawdust, wood, leaves, vegetables, nut shells, cotton waste, rice hulls, orange peels, poultry litter, paper sludge, sewage sludge, straw, distillers grain, or any combination thereof.

10. A method comprising:
   a) introducing a feedstock to an anerobic digestion process to generate at least a biogas effluent comprising methane, wherein the feedstock comprises biomass and optionally supplemental bio-derived material, wherein the biomass comprises harvested biodiverse above-ground plant material comprising at least about 10, 12, 15 or 20 different species of plants from a prairie or grassland; wherein the biodiverse above-ground plant material is harvested no more than one, two, or three times in a 12 month period of time; and wherein harvesting the biodiverse above-ground plant material no more than one, two, or three times in a 12 month period of time stimulates sequestration of atmospheric CO2 in soil of the prairie or grassland;
   b) passing a stream comprising oxygen and at least a portion of the biogas effluent to a methane conversion process operating at methane conversion conditions to generate a syngas stream comprising $CO_2$, CO, and $H_2$;
   c) passing the syngas stream to a microbial gas fermentation process comprising at least one C1 fixing microorganism and a nutrient solution in at least one bioreactor;
   d) culturing the C1 fixing microorganism in the bioreactor by fermentation to generate a fermentation broth comprising at least one chemical product;
   e) separating the at least one chemical product from the fermentation broth; and
   wherein the anerobic digestion process, the methane conversion process, and the microbial gas fermentation process are located within 1 mile, within 2 miles, within 3 miles, within 4 miles, or within 5 miles of one another.

11. The method of claim 10 wherein the supplemental bio-derived material is animal waste, agricultural waste, forestry waste, sewage, food waste, residential compost, industrial compost or any combination thereof.

12. The method of claim 10 wherein the ratio of biodiverse biomass and supplemental bioderived material varies according to when the biodiverse biomass is harvested.

13. The method of claim 10 wherein the feedstock does not undergo a drying procedure before the introducing to an anerobic digestion process.

14. The method of claim 10, wherein the C1-fixing microorganism is aerobic or anaerobic.

15. The method of claim 10, wherein the at least one product is selected from an alcohol, an acid, a diacid, an alkene, a terpene, an isoprene, and an alkyne.

16. The method of claim 10 wherein the harvested biodiverse above-ground plant material generates Carbon Emission Reduction Credits.

\* \* \* \* \*